(12) United States Patent
Gibson-Horn et al.

(10) Patent No.: US 8,215,773 B2
(45) Date of Patent: Jul. 10, 2012

(54) WEIGHTING GARMENTS AND ORTHOTICS FOR IMPROVING BALANCE

(75) Inventors: Cynthia Gibson-Horn, Oakland, CA (US); David Pearson, Thousand Oaks, CA (US)

(73) Assignee: Motion Therapeutics, Inc., Oakland, CA (US)

( * ) Notice: Subject to any disclaimer, the term of this patent is extended or adjusted under 35 U.S.C. 154(b) by 96 days.

(21) Appl. No.: 12/861,236

(22) Filed: Aug. 23, 2010

(65) Prior Publication Data

US 2011/0043755 A1 Feb. 24, 2011

Related U.S. Application Data

(60) Provisional application No. 61/325,981, filed on Apr. 20, 2010, provisional application No. 61/236,029, filed on Aug. 21, 2009.

(51) Int. Cl.
*A61B 3/00* (2006.01)
*A61B 3/14* (2006.01)
(52) U.S. Cl. ........................................ 351/203; 351/208
(58) Field of Classification Search .......... 351/200–246; 2/102
See application file for complete search history.

(56) References Cited

U.S. PATENT DOCUMENTS

| | | | |
|---|---|---|---|
| 4,122,840 A | 10/1978 | Tsuchiya et al. |
| 4,268,917 A | 5/1981 | Massey |
| 4,382,302 A | 5/1983 | Watson |
| 4,562,464 A | 12/1985 | Kurihara |
| 4,602,387 A | 7/1986 | Zakrzewski |
| 4,658,442 A | 4/1987 | Tomlinson et al. |
| 4,738,269 A | 4/1988 | Nashner |
| 4,971,073 A | 11/1990 | Schneider |
| 4,971,305 A | 11/1990 | Rennex |
| 4,989,267 A | 2/1991 | Watson |
| 5,002,270 A | 3/1991 | Shine |
| 5,052,406 A | 10/1991 | Nashner |
| 5,067,484 A | 11/1991 | Hiemstra-Paez |
| 5,120,288 A | 6/1992 | Sinaki |
| 5,144,694 A | 9/1992 | Conrad Da oud et al. |
| 5,209,240 A | 5/1993 | Jain et al. |
| 5,388,591 A | 2/1995 | De Luca et al. |
| 5,476,103 A | 12/1995 | Nahsner |
| 5,553,322 A | 9/1996 | Cebo-Johnson |

(Continued)

FOREIGN PATENT DOCUMENTS

GB 2129281 5/1984

(Continued)

OTHER PUBLICATIONS

International Search Report issued for PCT/US2010/046299, dated Nov. 15, 2010 (2 pages).

(Continued)

*Primary Examiner* — Mohammed Hasan
(74) *Attorney, Agent, or Firm* — Marcus C. Dawes; Daniel L. Dawes

(57) ABSTRACT

Weighting garment and orthotics are provided for improving balance. In particular, adjustable balance evaluation systems are used to determine placement of a weight to improve a subject's balance. These evaluation systems may be used to create customized garments for enhancing or improving balance. Described herein are customized garments for enhancing balance. Methods of creating customized garments enhance balance from the adjustable balance evaluation systems. Methods and apparatus further include eyeglasses with weights and testing methods to improve vision.

20 Claims, 33 Drawing Sheets

U.S. PATENT DOCUMENTS

| | | | |
|---|---|---|---|
| 5,582,583 | A | 12/1996 | Ballantyne |
| 5,659,898 | A | 8/1997 | Bell, Jr. |
| 5,713,840 | A | 2/1998 | Brentham |
| 5,799,328 | A | 9/1998 | Harlem et al. |
| 5,810,699 | A | 9/1998 | Nadeau |
| 5,937,441 | A | 8/1999 | Raines |
| 5,943,700 | A | 8/1999 | Hammer et al. |
| 5,951,446 | A | 9/1999 | Monforte |
| 5,957,873 | A | 9/1999 | Allen |
| 5,978,964 | A | 11/1999 | Gaston |
| 6,005,041 | A | 12/1999 | Cook |
| 6,010,465 | A | 1/2000 | Nashner |
| 6,056,671 | A | 5/2000 | Marmer |
| 6,056,674 | A | 5/2000 | Cook |
| 6,081,924 | A | 7/2000 | Ott |
| 6,113,521 | A | 9/2000 | Winston |
| 6,200,243 | B1 | 3/2001 | Meranto |
| 6,200,244 | B1 | 3/2001 | Cook |
| 6,209,135 | B1 | 4/2001 | Irvin |
| 6,244,997 | B1 | 6/2001 | Cook |
| 6,248,043 | B1 | 6/2001 | Morton |
| 6,314,580 | B1 | 11/2001 | Greenberg et al. |
| 6,364,851 | B1 | 4/2002 | Nafpliotis |
| 6,554,752 | B2 | 4/2003 | Cook |
| 6,557,176 | B2 | 5/2003 | Franco-Sion |
| 6,675,391 | B2 * | 1/2004 | Morrison ............................ 2/102 |
| 6,692,413 | B1 | 2/2004 | Greenberg et al. |
| 6,788,968 | B2 | 9/2004 | Pettibon |
| 7,156,792 | B2 | 1/2007 | Gibson-Horn |
| 7,775,663 | B2 * | 8/2010 | Andino et al. ................. 351/212 |
| 2002/0152534 | A1 | 10/2002 | Morrison |
| 2002/0169376 | A1 | 11/2002 | Pettibon |
| 2003/0186789 | A1 | 10/2003 | Cook |
| 2006/0000478 | A1 | 1/2006 | Taylor |
| 2007/0161875 | A1 | 7/2007 | Epley |

FOREIGN PATENT DOCUMENTS

| | | |
|---|---|---|
| SE | 218063 | 1/1968 |
| WO | WO-9847450 | 10/1998 |
| WO | WO-2004-066821 | 8/2004 |

OTHER PUBLICATIONS

Anonymous (2002). "Full Catalog with Pictures and Descriptions," Online! Spinal Technologies located at http://www.spinal-Tech.com/order/Catalog2002.pdf (20 pages), 2002.

Author Unknown, "The Pettibon System: Proven Spine and Posture Correction," 8 pages, retrieved from http://images.vortala.com/chiropractor/USA/Maryland/Rockville/THE%20Spinal%20Correction%20and%20Wellness%20Center/SiteGraphics/headweight%20instructions, 2002.

Bastian, A.J. (Jun. 1997), "Mechanisms of Ataxia," Phys. Ther. 77(6):672-675.

Chase, R.A. et al. (May 1, 1965), "Modification of Intention Tremor in Man," Nature 206(4983): 485-487, 4 pages.

Clopton, N. et al. (Mar. 2003), "Effects of Axial Weight Loading on Gait for Subjects with Cerebellar Ataxia: Preliminary Findings," Neurology Report 27(1): 15-21.

Frank, J.S. and Earl, M. (1990), "Coordination of Posture and Movement," Physical Therapy 70(12):855-863.

Gillen, G. (Jan./Feb. 2000), "Improving Activities of Daily Living Performance in an Adult with Ataxia," The American Journal of Occupational Therapy 54(1):89-96, 10 pages.

Hewer, R.L. et al. (1972), "An Investigation into the Value of Treating Intention Tremor by Weighting the Affected Limb," Brain 95(Part IV):579-590, 14 pages.

Holmes, G. (Mar. 1939), "The Cerebellum of Man," Brain 62(1):1-30, 31 pages.

Horn, C.G., "Balance-Based Torso-Weighting in a Patient with Ataxia and Multiple Sclerosis: A Case Report," JNPT, vol. 32, Sep. 2008, pp. 139-146.

Horn, C.G. et al. (Aug. 2003), "Post Lower Extremity Fracture Study," Journal of Bone and Mineral Research 18(Suppl. 1):5278, 3 pages.

International Search Report mailed on Aug. 6, 2004, for PCT Patent Application No. PCT/US2004/002255 filed on Jan. 25, 2004, three pages.

Meyer, D., "A Brief History and Clinical Observations: Regarding the Use of Body Weighting for Postural/Structural Correction," The American Journal of Clinical Chiropractic, Jan. 2005, vol. 15, No. 1, 6 pages.

Morgan, M.H. et al. (1975), "Application of an Objective Method of Assessing Intention Tremor—A Further Study on the Use of Weights to Reduce Intention Tremor," Journal of Neurology Neurosurgery and Psychiatry 38:259-264, 7 pages.

Nashner, L. (1990), "Sensory, Neuromuscular and Biomechanical Contributions to Human Balance," Proceedings of the APTA Forum in Nashville, TN, American Physical Therapy Association: Alexandria, VA, pp. 5-12, 10 pages.

NeuroCom International, Inc. (1998), "Assessment of Balance and Mobility Functions: A Reference Population Study Based on the Balance Master 6.1," NeuroCom International, Inc., Clackamas, OR, pp. 1-31, 32 pages.

O'Sullivan, S.B. (2001), "Multiple Sclerosis," Chapter 22 in *Physical Rehabilitation: Assessment and Treatment*, O'Sullivan, S.B. et al., eds., Fourth Edition, F.A. Davis Company, Philadelphia, PA, pp. 715-741, 29 pages.

Pettibon, B., "Head Weighting System for Spinal Treatment Description/Claims," Patent Description & Claims from U.S. Patent Application No. 20070042869, 9 pages, retrieved from http://www.freshpatents.com/Head-weighting-system-for-spinal-treatment-dt20070222pta, retrieved on Aug. 16, 2010.

Pierce, et al., "Joint Pain? A Patient's Perspective: Is your head on straight?," UpC Spine—A New Approach, 3 pages, retrieved on Aug. 10, 2010 from http://www.upcspine.com/tech7.htm.

Schapiro, R.T., (1998), "*Symptom Management in Multiple Sclerosis,*" Third Edition, Demos Medical Publishing Co., Inc., New York, NY, pp. ix-x (Table of Contents Only), 4 pages, 1998.

Snow, C.M. et al., (Sep. 2000), "Long-Term Exercise Using Weighted Vests Prevents Hip Bone Loss in Postmenopausal Women," Journal of Gerontology 55A(9):M489-M491, 5 pages, 2000.

Widener, et al., "Balance-Based Torso-Weighting May Enhance Balance in Persons with Multiple Sclerosis: Preliminary Evidence," Arch Phys Med Rehabil, vol. 90, Apr. 2009, pp. 602-609, 9 pages.

Widener, et al., "Randomized Clinical Trial of Balance-Based Torso Weighting for Improving Upright Mobility in People with Multiple Sclerosis," Neurorehabilitation and Neural Repair, vol. XX, No. X, May 2009, 8 pages.

Woollacott, M.H. and Tang, P.F., (1997), "Balance Control During Walking in the Older Adult: Research and its Implications," Physical Therapy 77(6):646-660, 1997.

Written Opinion mailed on Aug. 6, 2004, for PCT Patent Application No. PCT/US2004/002255 filed on Jan. 1, 2004, six pages.

\* cited by examiner

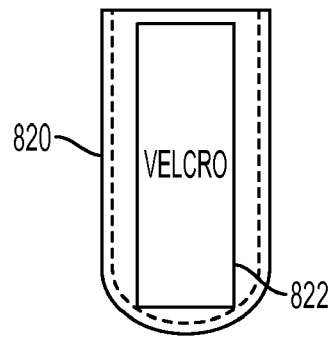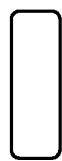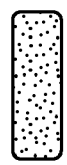
FIG. 8E　　　　FIG. 8F　　　　FIG. 8G
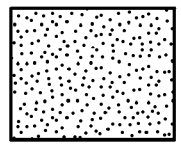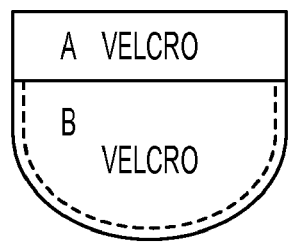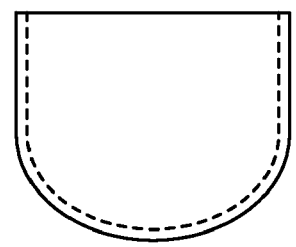
FIG. 8H　　　　FIG. 8I　　　　FIG. 8J

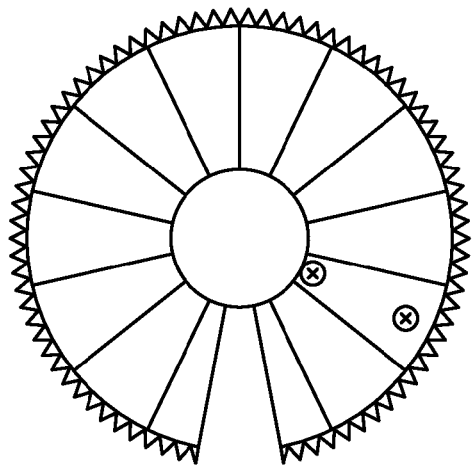
FIG. 26A
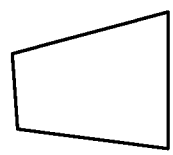   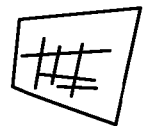   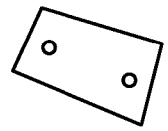
FIG. 26B      FIG. 26C      FIG. 26D
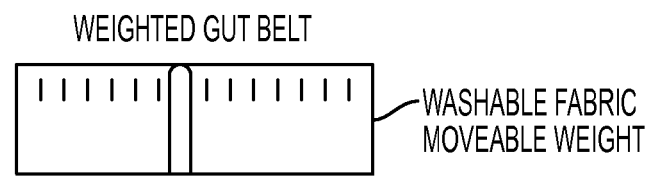
FIG. 27

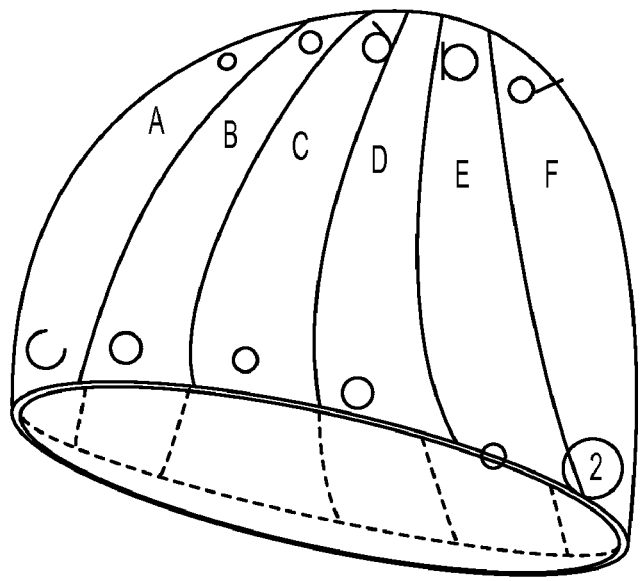
FIG. 28A
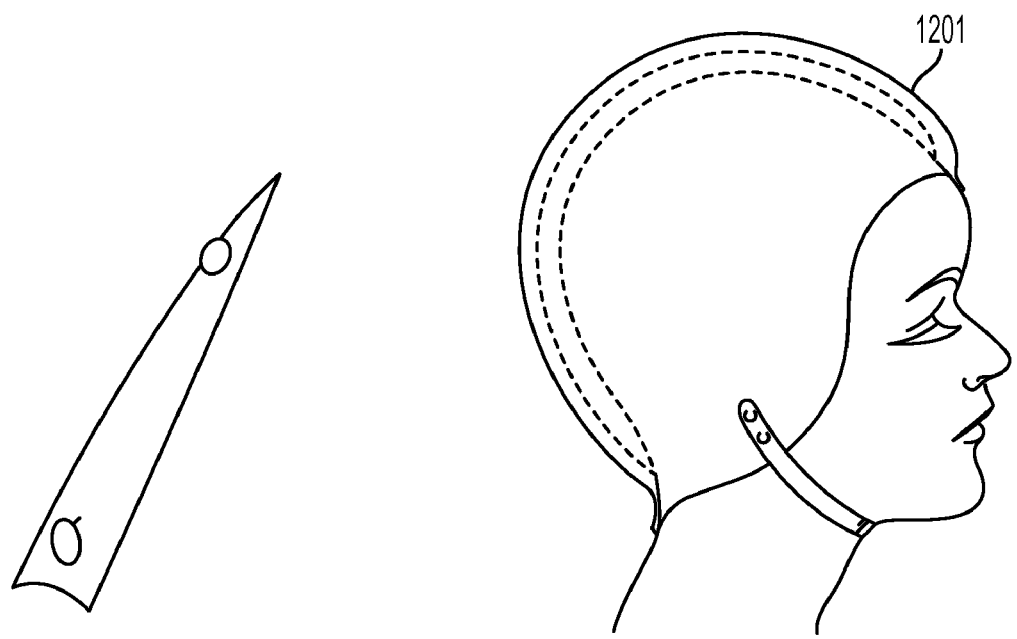
FIG. 28B                    FIG. 29

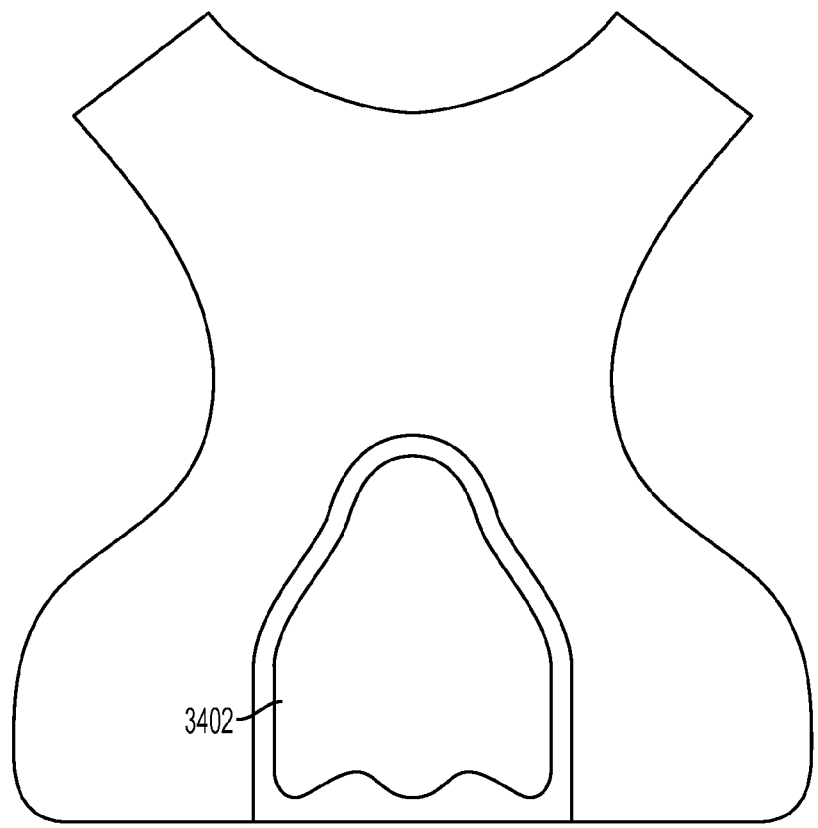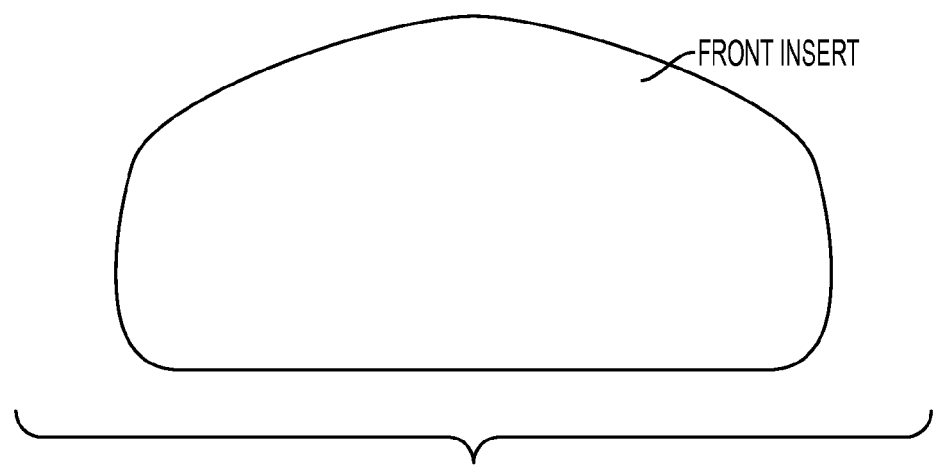
FIG. 34

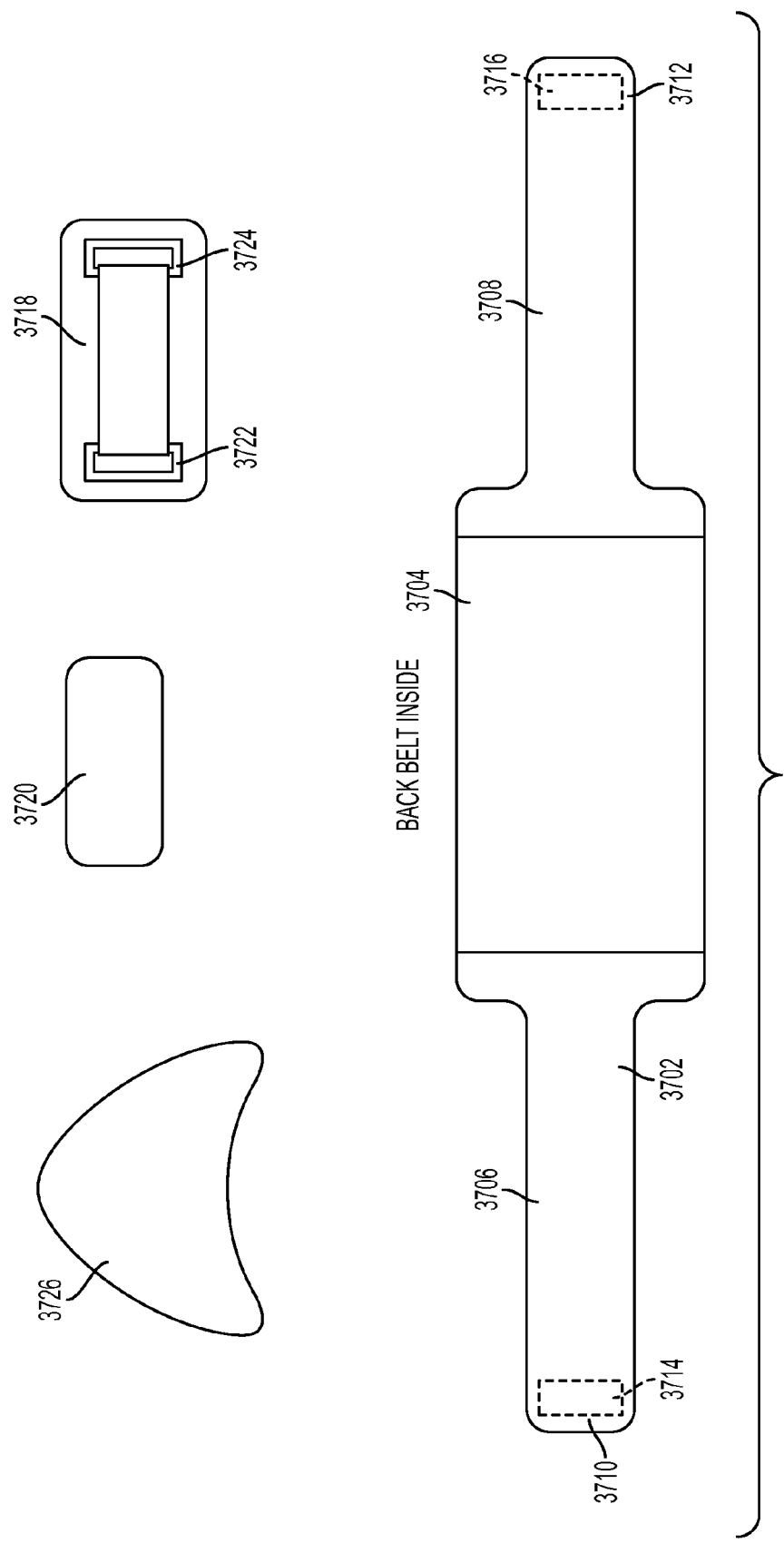

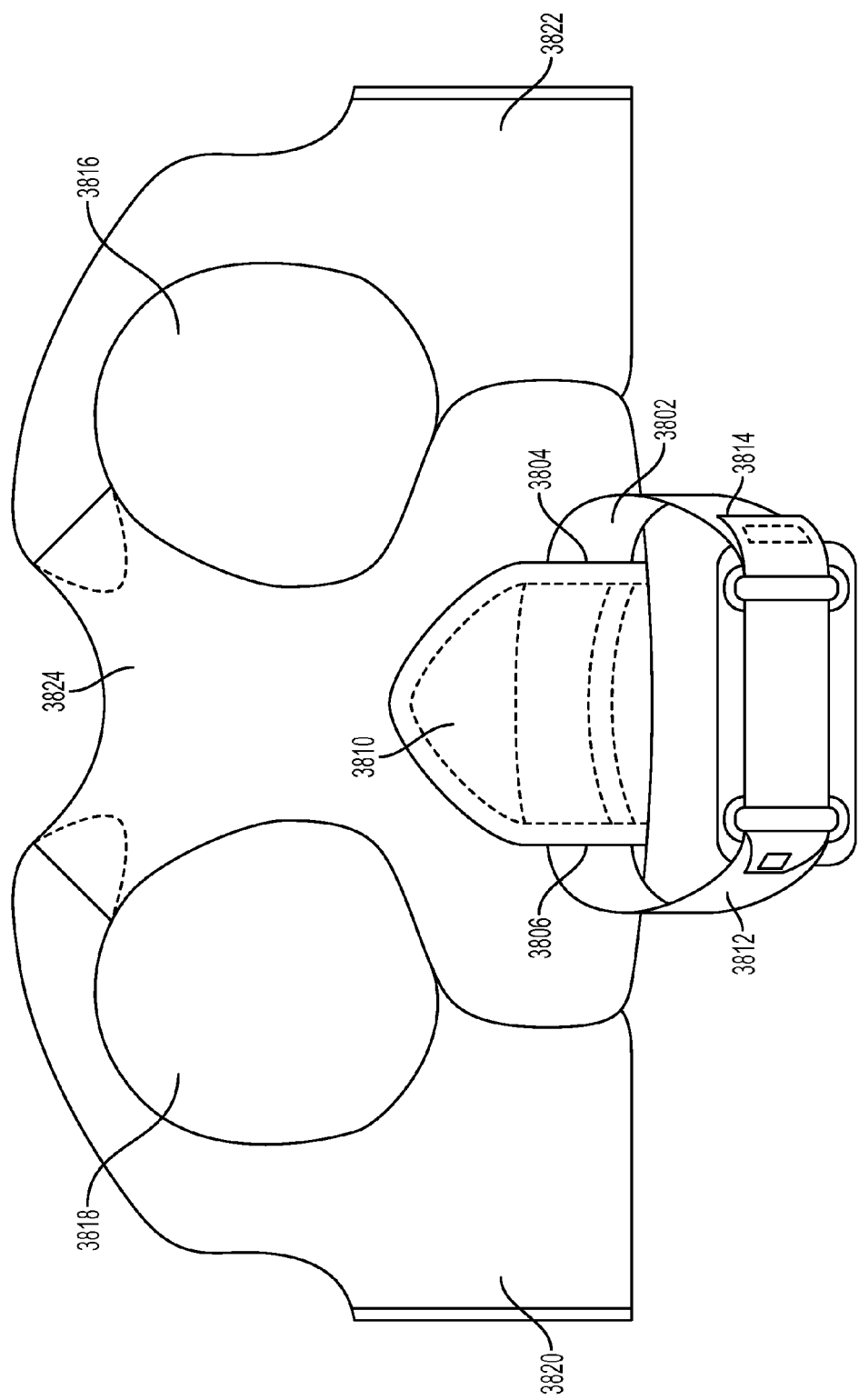

WEIGHTING GARMENTS AND ORTHOTICS FOR IMPROVING BALANCE

CROSS REFERENCE TO RELATED APPLICATIONS

This application claims priority to U.S. Provisional Application No. 61/325,981, filed Apr. 20, 2010, the contents of which are incorporated herein by reference. This application also claims priority to U.S. Provisional Application No. 61/236,029, filed Aug. 21, 2009, the contents of which are incorporated herein by reference.

This application has subject matter related to U.S. application Ser. No. 11/565,207, filed on Nov. 30, 2006, now U.S. Pat. No. 7,708,673, which is a continuation of U.S. patent application Ser. No. 10/353,539, filed on Jan. 28, 2003, now U.S. Pat. No. 7,156,792. U.S. Pat. Nos. 7,708,673 and 7,156,792 are both incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described here are weighted garment devices or orthotics, systems for making and using them, and methods for providing a patient having a balance disorder, or proprioceptive loss, with a weighted garment or orthotic device tending to improve the patient's balance. Garments and other devices produced using these methods are also shown.

BACKGROUND

Many individuals suffering from neurological disorders, balance dysfunction, difficulty with weight shifting, and loss of proprioception, have problems maintaining their center of gravity ("COG") over their base of support, the perimeter defining the contact region surrounding the feet. The inability to maintain one's COG over the base of support results in decreased postural and motor control in sitting, standing, changing positions, and locomotion. Maintenance of the COG over the base of support is desirable for smooth and coordinated movement in balance and gait.

The ability to maintain COG balance over the base of support relies in part on three input systems: the somatosensory (proprioceptive and tactile input from the torso, feet, and ankles); the vestibular (spatial orientation and balancing functioning); and the visual (input from sight). When a problem occurs in one of these input systems, it may affect both the input to the sensory integration system of the central nervous system ("CNS") and the resulting ability to use the remaining one or more of the somatosensory, vestibular, or visual input systems for balance. The CNS may then tend to rely more heavily on one input system relative to another, or even to rely on other areas of the nervous system itself. Changing the input to one system may allow another system to function normally.

The nervous system's reliance on other areas of the CNS to compensate for the deficiency of one input system can lead to nervous system fatigue. In addition, problems associated with ineffective or inaccurate input or output tend to affect motor control, speed, movement coordination, automatic postural reaction, ability to control one's COG over their base of support, weight shifting, equal weight bearing, vision, cognition, and equilibrium. Alterations in input and output systems vary with age, with the type and severity of the neurological problem, and with the severity of any resulting neurological degeneration.

Proper coordination of posture and movement rely on the body's ability to initiate and effect subtle postural adjustments. For example, one's ability to remain in an upright position while sitting or standing is fundamental to safe and efficient movement. Similarly, balance control while walking requires proactive control of upper body stability in both the sagittal, frontal, and transverse planes, as well as the coordination of the upper and lower extremities. Such control is often compromised due to various neurological disorders and aging. Correction of aberrant balance is often complicated by the biomechanics of certain movements.

For example, two-thirds of a human's body weight is centered in the upper body (head, torso, and arms). When the body mass is not neutral, or is off-center, the center of gravity is not positioned over the base of support. This is simply a natural instability due to the anatomy of a human being. However, when a person cannot maintain control over this natural instability, decreased ability in function, cognition, coordination, balance, ambulation, vision, and equilibrium tend to occur. To ameliorate and/or eliminate this instability and facilitate better movement, I have found that providing certain counterbalances and proprioceptive cues to a person having such a problem tends to overcome upper body instability and allow improve function of the above-mentioned systems.

SUMMARY

The present invention relates to adjustable balance evaluation garments, methods of using them to determine where on the garment to place a weight to enhance a subject's stability, customized adjustable and non-adjustable garments to enhance balance, and methods of making customized adjustable and non-adjustable garments to enhance balance, vision, and equilibrium.

For example, described herein are methods of making customized non-adjustable garments or orthotics comprising the steps of: placing a first weight on an adjustable balance evaluation garment to determine where on the adjustable balance evaluation garment to place a weight to enhance the subject's stability; and securing a corresponding weight to a customizable garment in the position identified from the adjustable balance evaluation garment. The weight combination may be less than 2% of the subject's body weight.

In some variations, the weight is permanently secured to the customizable garment. For example, the weight may be sewn to the fabric of the garment or sewn within the garment, or the fabric may be secured to the garment so that the fabric itself may provide the weight (i.e., weighted or heavy fabric).

Also described herein are customized non-adjustable orthotic garments for improving the balance of a subject for whom the garment is made, the garment comprising: a garment body configured to be worn by a subject; and a weight secured to the garment body in a position that is not symmetric relative to the subject's body; wherein the weight corresponds to between about 0.2% and 2% of the subject's body weight. The weight may correspond to between about 0.5% and about 1.5% of the subject's body weight. The garment body may be configured to fit over the subject's torso or other body part. In some variations, the garment body is configured as an undergarment. The garment body may be configured to be worn on a head or limb or as a vest, shirt or jacket.

Also described herein are adjustable balance evaluation systems for aligning a patient's ("patient" and "subject" are used interchangeably in this disclosure) COG over their base of support, the system comprising: a belt strap configured to attach a weight at a non-predetermined position along the length of the belt strap, wherein the belt strap comprises markings to indicate the location of an attached weight; a shoulder strap configured to connect to the belt strap, wherein the shoulder strap is configured to attach a weight at a non-predetermined position along the length of the shoulder strap, further wherein the shoulder strap can, but need not, comprise markings to indicate the location of an attached weight; and a repositionable weight configured to be positioned on the shoulder strap or belt strap, wherein the weight combination is less than about 4 pounds. The system may also include a weight packet for holding the weight and attaching to the belt or shoulder strap. In some variations, the system also includes a clip for attaching to the end of the shoulder strap and coupling the strap to the belt strap.

The system may include a pair of shoulder straps. Alternatively, the shoulder strap may comprise a back strap and a pair of front straps extending from the back strap. The belt strap and the shoulder strap may comprise a Velcro-type attachment material.

The repositionable weight may be less than 4 pounds, less than 3 pounds, or less than 2 pounds. In some variations, a plurality of repositionable weights may be used.

Also described herein are adjustable balance evaluation systems for aligning a patient's COG over their base of support, the system comprising: a belt strap configured to attach a weight at a non-predetermined position along the length of the belt strap, wherein the belt strap comprises markings to indicate the location of an attached weight; and a plurality of repositionable weights configured to be positioned on the belt strap, wherein the weights are less than about 3 pounds.

Also described are adjustable balance evaluation systems for aligning a patient's COG over their base of support, the system comprising: a wearable garment having a weight attachment surface configured to attach a weight at a non-predetermined position on the weight attachment surface, wherein the weight attachment surfaces comprises markings to indicate the location of an attached weight; and a plurality of repositionable weights configured to be positioned on the wearable garment, wherein the weights are less than about 3 pounds. The wearable garment may be configured as a shirt, vest, or jacket. In some variations, the wearable garment is configured as a cap, headband, or hat.

Also provided herein are methods and devices for assisting a person having a balance disorder in need of such assistance, or for aligning a person's COG over their base of support biomechanically or proprioceptively (e.g., by receiving stimuli originating in muscles, tendons, and other internal tissues). Improvements in the ability to think (cognate), see, use eyes, sit, stand, turn, walk, shift weight, coordinate, and balance may be achieved. The methods and apparatuses described here are suited to individuals suffering from various neurological disorders and orthopedic conditions. For example, persons suffering from cerebellar degeneration, Parkinson's disease, multiple sclerosis, age-related degenerative disorders, stroke, traumatic injury to the head, brain, or spinal cord, orthopedic injury, and cerebral palsy, may benefit from my described methods and apparatuses.

One described method provides an assessment of a patient's need for a selectively weighted garment or orthotic and for determining the proper weight placement within or upon the weighted garment or orthotic. These methods may be manual, e.g., observational, and/or to some degree computer-assisted. Video recording equipment or other electronic equipment may be used.

For example, these methods may comprise the steps of observing a patient's ability to maintain their COG over their base of support, optionally perturbing the patient (e.g., by applying an external push or by having the patient try to resist the movement force, etc.) and observing their body's reaction to the perturbation, selectively weighting the patient's torso, head, or limb, and observing the patient's ability to maintain their COG over their base of support after being weighted. Additional steps may include temporarily reducing or eliminating the patient's vision and observing the patient's ability to maintain their COG over their base of support, and recording the position and value of each weight secured to the garment or orthotic. Any or all of the steps may be repeated as necessary. In addition, these methods may be computer assisted.

The present invention includes weighted garments or orthotics, typically produced using procedures described here. These garments or orthotics may take on any number of configurations. The garment or orthotic may be a vest, perhaps having at least one pocket for receiving and securing a weight therein, or may have a plurality of pockets. The pockets may be distributed throughout the vest in a plurality of orientations and have a plurality of sizes. The weighted garment or orthotic may also be a head piece, collar, brassiere, corset, shoulder pad, belt, seating device to be used in combination with a wheelchair, tee shirt, body suit, undergarment, or combination thereof. Functionally, the weighted garments are of a form, size, shape, and thickness, suitable for correcting, assisting in or alleviating at least a portion of a patient's balance dysfunction.

The garment or orthotic may have pockets, receptacles, or tubes for placement of weights therein or thereupon. The garment or orthotic may be weighted in a distribution pattern determined by the methods of the present invention, or the material making up the garment or orthotic may be the weighted medium.

One garment of particular utility is a coat, vest, or shirt constructed in such a way that it has a number of elastic tubes situated along the body when worn. The tubes themselves may have openings at each end and at points intermediate in the tubes for introduction of weights or stimuli at various positions within the tubes. Other garments of interest include undergarments such as brassieres, corsets, shoulder pads, belts, seating devices and the like that, if desired, may be used in combination with a wheelchair, tee shirts, undergarments, body suits, and combinations thereof.

The apparatuses, garments, and orthotics of the present disclosure can also include one, two, or more than two relatively rigid inserts that support the back, torso, or neck. An insert can be enclosed in a pocket on the back of the garment. The pocket can be sealed by a variety of ways, including, but not limited to, hook and loop material, buttons, zippers, and the like. The garments may be of unitary design or be made of multiple components. The garments or apparatuses can also include a belt. The belt can wrap around the outside of the insert through openings in the garment or apparatus. The belt can also include another insert.

This disclosure is also directed to methods for improving a subject's vestibular system. In these methods, a subject's vestibular system is initially evaluated. Next, the subject's vestibular system is stimulated by one or more weights or stimuli on the head, neck, or torso. Then, the subject's vestibular system is evaluated again. If, when compared to the initial evaluation of the vestibular system, the subject's vestibular system does not show improvement, the one or more stimuli and/or devices applied to the subject's vestibular system can be adjusted or added to. These steps of comparing and adjusting or adding to the one or more stimuli or devices are repeated until the subject's vestibular system shows improvement when compared to the initial evaluation.

This disclosure also includes methods and apparatuses for improving a subject's vision. The apparatuses can include eyeglasses or eyeglass frames that can be weighted, symmetrically or asymmetrically. In these methods, a subject's vision is initially evaluated. After the initial evaluation, a person's vestibular or ocular system is stimulated by one or more stimuli or devices, such as by providing weights on or within eyeglasses or eyeglass frames, or via application of stimuli to the torso. If, when compared to the initial evaluation of the subject's vision, the subject's vision does not show improvement, the one or more stimuli and/or devices applied to the subject's vestibular system can be adjusted or added to. These steps of comparing and adjusting or adding to the one or more stimuli or devices are repeated until the subject's vision shows improvement when compared to the initial evaluation.

Other features and advantages will become apparent from the following description, drawings, and claims.

BRIEF DESCRIPTION OF THE DRAWINGS

In FIG. 6A the patient is unweighted, while in FIG. 6B the patient is wearing a weighted garment as described herein.

FIGS. 7A and 7B show variations from the front, and FIGS. 7C-7E show variations from the back.

FIG. 8E shows one variation of a weight packet, as described herein, and FIG. 8F illustrates a weight which may be used with such a weight packet.

FIG. 8G shows another variation of a weight, in which the weight includes an attachment means (e.g., securely attached to the weight).

FIG. 8H is a generic example of a fastener that may be used with the adjustable balance evaluation tool (system) shown in FIGS. 8A-8D, and FIGS. 8I and 8J show front and back perspective views, respectively, of one variation of a fastener that may be used to link the straps (e.g., FIGS. 8C-8D) to the belt portion (FIGS. 8A-8B).

FIG. 26A is an adjustable balance evaluation tool configured as a collar. FIGS. 26B-26D illustrate variations of weights and weight packets that may be used with the weighted collar shown in FIG. 26A.

FIG. 27 illustrates another variation of an adjustable balance evaluation tool configured as a belt.

FIG. 28A shows an adjustable balance evaluation tool configured as a hat or cap. FIG. 28B shows one variation of an adjustable-position weight for use with the adjustable balance evaluation tool shown in FIG. 28A.

FIG. 29 shows another variation of an adjustable balance evaluation tool configured as a cap.

FIGS. 34-38 are various views of additional embodiments including a relatively rigid support component.

DETAILED DESCRIPTION

Described herein are methods for assessing a need for a weighted garment or orthotic and for determining appropriate weight and weight placement within the garment or orthotic. In addition, described herein are tools for performing these methods, including adjustable balance evaluation tools (devices and systems). An adjustable balance evaluation tool may be a weighted garment or orthotic. In some variations, the adjustable balance evaluation tool may be used to create a therapeutic device such as a weighted garment or orthotic that is not adjustable. The methods described herein may variously be manual, computer-assisted, or combinations of the two.

Figure 1:
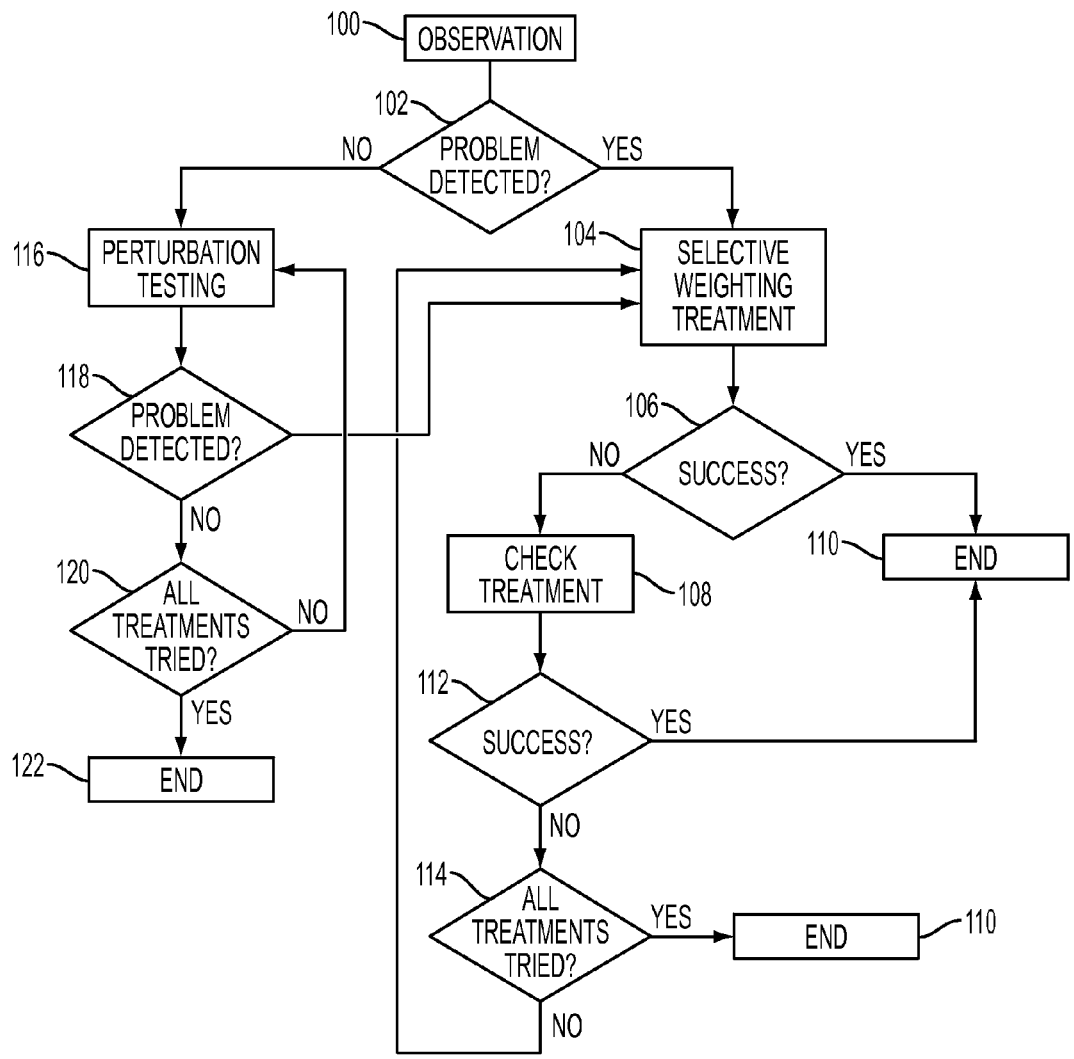
FIG. 1 provides a general flowchart of a method of weighting a garment or orthotic to improve a user's balance.

Making reference now to the drawings, FIG. 1 is a general overview of a method for assessing a need for a weighted garment or orthotic and for determining an appropriate weight and weight placement within that garment or orthotic.

In general, these methods make use of body positioning and perturbation techniques to detect balance dysfunction. When a balance dysfunction is identified, the method of the present invention may be used to systematically and selectively apply weight to the patient's torso or other body region. In general, a weight is selected for placement on or within the therapeutic garment or orthotic. The size may depend on, inter alia, the patient's tolerance for the weight and their treatment needs. Typically, the various weights applied to the garment range from ¼ pound to 5 pounds for adults, or less than that for children, for example, 1-3% of a patient's body weight. The determination of the appropriate weight may further be dependent upon on the patient's size, strength, and resistance to move the patient's COG to the center of the base of support. For example, the weight applied may be less than 2.5% of the patient's body weight, less than 2% of the patient's body weight, less than 1.5% of the patient's body weight, or the like. These weights are generally much lighter than weights used in other therapeutic or exercise weighting systems. For example, the weights used to achieve compression of joints (i.e., to get joint stabilization) are typically much greater than the four pounds or less than four pound weights used in the methods, devices and systems described here.

In accordance with the methods described herein, continued perturbation and balance testing is done until the patient resists the perturbation or shows improvement in control or movement compared to the initial observations, or (ideally) evidences improvement in control and movement that cannot be further maximized. After an appropriate weight placement has been determined, changes in movement control, walking ability, cognition, vision, or dizziness may be assessed. The patient may, during the procedure, be asked about their ability to tolerate additional weight and their overall comfort level with the weighted apparatus. In this way, the amount of weight may be modified prior to the final preparation of the weighted apparatus if necessary.

In its most elemental form, this procedure is observational and heuristic. This procedure does not necessarily rely on specific balance standards for assessing the magnitude of a patient's balance dysfunction (e.g., Berg balance standards, Tinetti balance standards, posturography, etc.). The assessment of a patient's improvement during this described procedure is by observation following the various instructions given here, or may be had by monitoring a patient's COG placement after introduction of a specific weight at a specific site and comparing it to a comparable COG before that treatment step. Depending upon the malady and the patient, the appropriate treatment may result in placement of a weight on the side of the patient considered likely to move the COG further toward center, biomechanically or proprioceptively.

As shown in FIG. 1, the first step 100 is an initial observation of the patient. In this step the patient's physical orientation is observed. This usually involves observation of the patient while sitting or standing, while the provider observes the patient's frontal, sagittal, or transverse plane orientation, as well as bodily movements and balance dysfunction cues. The sagittal plane refers to the imaginary vertical plane through the body that divides the body into equal left and right halves. The frontal, or coronal plane, refers to the imaginary plane through the body that separates the front from the back.

For example, during observation, the patient may first be observed in a sitting orientation. The observation may involve the exploration of following questions: 1) is the patient able to sit upright without support?; 2) if the patient is unable to sit upright without support, which way does the patient tend to fall or lean?; 3) is the patient sitting with their body positioned in the midline of the coronal and sagittal planes?; 4) which way does the patient lean?; 5) what happens to the patient when they close their eyes (e.g., do they lean in a different direction, sway more, etc.)? If the patient is unable to sit without support for example, or there are other indications or cues that the patient has a balance dysfunction, the selective weighting process 104 may begin.

The patient may also be observed in a standing orientation. For example, the observation may involve the exploration of the following questions: 1) how does the patient get from the sitting to the standing positions (e.g., is this movement smooth; do they use their hands, etc)?; 2) can the patient stand without use of their hands?; 3) how many attempts does it take the patient to stand?; 4) how stable is the patient's initial standing balance (e.g., do they sway; how far apart are the patient's feet, etc.)?; 5) can the patient stand with feet together without falling?; 6) how many steps does it take for the patient to bring the feet together?; 7) does the patient falter while standing?; 8) what happens to the patient when they close their eyes (e.g., do they lean in a different direction, sway more, etc.). If the patient is unable to stand without support, or there are other indications or cues that the patient has a balance dysfunction, the selective weighting process 104 may begin.

The observation step 100 may also include observation of gait. For example, observation of gait may involve the exploration of the following questions: 1) is there a disturbance in the swing or stance phases of gait?; 2) does the patient have equal stride lengths?; 3) is there any hyperextension at the knee?; 4) does the patient scuff their foot while they walk?; 5) can the patient walk a straight line?; 6) does the patient lose their balance while walking (e.g., while walking straight, forward, or turning, etc.)?; 7) How is the vestibular ocular system functioning (e.g., how does the patient perform when walking and turning the head or eyes)?

In general, the observation may take any number of forms and includes all methods of observation useful in acquiring data. For example, the observation step may take the form of visual observation and may include the use of mechanical or electronic aids. Video recording equipment may be used to aid in observation step 100. In addition, it is often useful to first offset the patient's balance by physical perturbation during the observation step 100. Such perturbation may, for example, include applying one or more slight external forces to the patient, perhaps from a number of different directions.

This type of perturbation testing is analogous to the perturbation testing done in step 116 and will be discussed in greater detail below.

That is, if after initial observation, no problem has been detected 102, perturbation step 116 may be performed. The detection of a problem 102 is based in large part on the observation of the patient's orientation and exploration of the questions highlighted above (or similar such questions). Perturbation step 116 may occur while the patient is in any given position (e.g., sitting or standing) and any number or types of perturbation forces may be applied to the patient.

For example, an anterior posterior perturbation force may be applied to the patient, wherein the patient receives a horizontal force to the sternum in a posterior direction. If the patient falls or leans backwards, this is termed a "posterior balance dysfunction." Similarly, a posterior anterior perturbation force may be applied to the patient, wherein the patient is pulled forward horizontally by both hands. If the patient falls or leans forward, this is termed an "anterior balance dysfunction." The patient may also be subjected to a lateral perturbation, wherein a force is directed laterally through the humerus at the top of the shoulder joint to displace the patient sideways, to the right or the left. If the patient falls or is unable to resist the perturbation, this is termed a "lateral dysfunction." Each of these dysfunctions may further be classified as "to the right" or "to the left" based on the direction the patient is unable to resist the perturbation.

The patient may also be subjected to a rotational perturbation. In a right rotational perturbation, the right shoulder of the patient is pulled forward and the left shoulder is pushed back. Similarly, in a left rotational perturbation, the left shoulder of the patient is pulled forward and the right shoulder of the patient is pulled back. If the patient exhibits less control over their right shoulder being pulled forward than their left shoulder, this is termed a "right rotation dysfunction." Conversely, if the patient exhibits less control over their left shoulder being pulled forward than their right shoulder, this is termed a "left rotation dysfunction."

However, as mentioned above, if during observation 100, a problem is detected 102, selective weighting treatment 104 may begin. The selective weighting step 104 involves the placement of individual weights on the torso to aid the patient in counteracting the displacement of COG over the base of support via biomechanical or proprioceptive input. At this stage, any method may be used to place the weights on the patient's torso. For example, the patient may be provided with a vest or other garment, or the weights may be placed on the patient's torso through any other method.

If a vest is used, for example, the vest may contain a number of pockets or receptacles for receiving weights. The vest may contain a plurality of pockets, having various sizes and orientations. In this way, weight placement along the torso's superior, posterior, lateral, or anterior directions, or any combinations thereof, may be assessed.

Figures 6A, 6B:
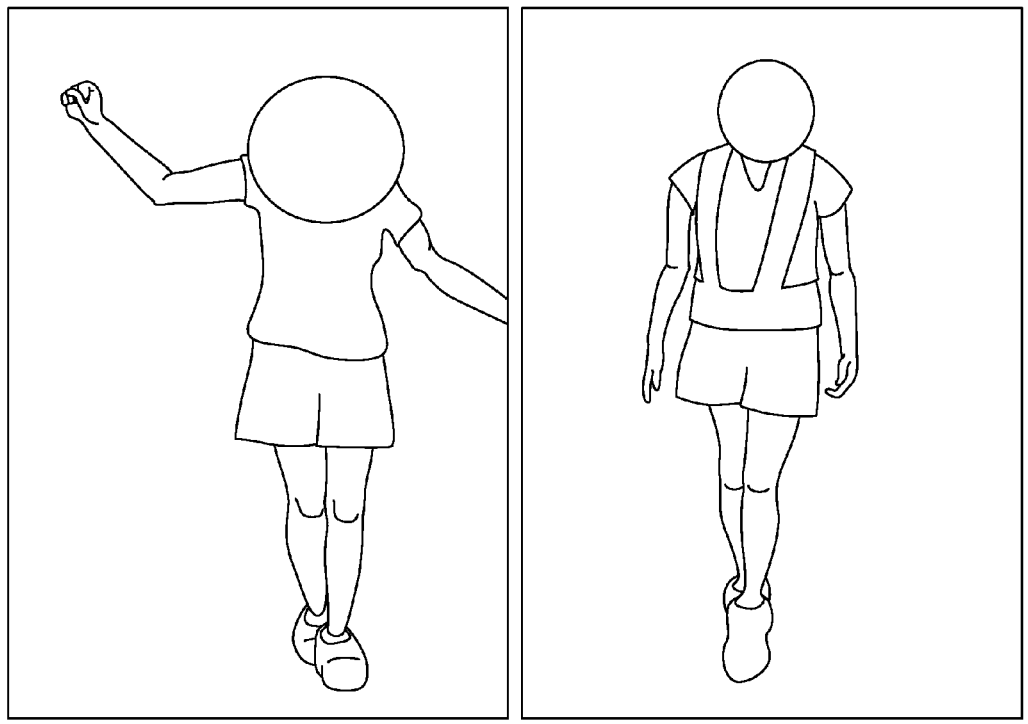
FIGS. 6A and 6B illustrate to effect of weighting on a patient.

In practice, the methods described herein have shown remarkable success. For example, FIGS. 6A and 6B illustrates a patient with multiple sclerosis who experiences difficulty in balancing before (FIG. 6A) and after (FIG. 6B) weighting as described above. In FIG. 6A the patient is asked to perform a tandem stance walking behavior (e.g., walking toe-to-toe) while balancing herself. During performance of the task her she had difficulty maintaining her balance, resulting in rapid and erratic arm swinging, as illustrated. After determining the positioning and weighting, as described above, she was provided with a single ½ lb weight located near her right shoulder blade, on the back of an adjustable balance evaluation tool worn over her torso, as illustrated in FIG. 6B. The adjustable balance evaluation tool in this example has two shoulder straps that attach to a waist band. A weight may be secured in any position on this adjustable balance evaluation tool; in this variation one surface is a hook material, which can mate with a hook material secured to the weight (e.g., a Velcro-type interaction). In FIG. 6B the patient is shown performing the same task (e.g., walking in a tandem stance) with substantially better balance.

In general, if an adjustable balance evaluation tool is used, such as a vest, including the garments/systems illustrated in FIGS. 2A-2B and FIGS. 4A-5C, the weights may be placed in any position on the adjustable balance evaluation tool, rather than pre-determined positions. Thus, as described in greater detail below, the adjustable balance evaluation tool may allow for weights to be positioned in regions immediately adjacent or continuously adjustable positions.

The weights may be flexible or rigid, and have any given thickness. The garment (the adjustable balance evaluation tool) may be marked (e.g., on the pockets, receptacles or surface of the garment receiving the weight(s) to allow recordation of the weight placement. For example, pockets or receptacles may be numbered, or may be designated with alphabetic characters, symbols, pictures, figures, or any combinations thereof. Thus, pockets of an adjustable balance evaluation vest may be numbered and the method of weighting the orthotic identified and results recorded using a numbering system. Alternatively, recordation of the weight placement may be made on an exam form or sheet.

Figure 2A:
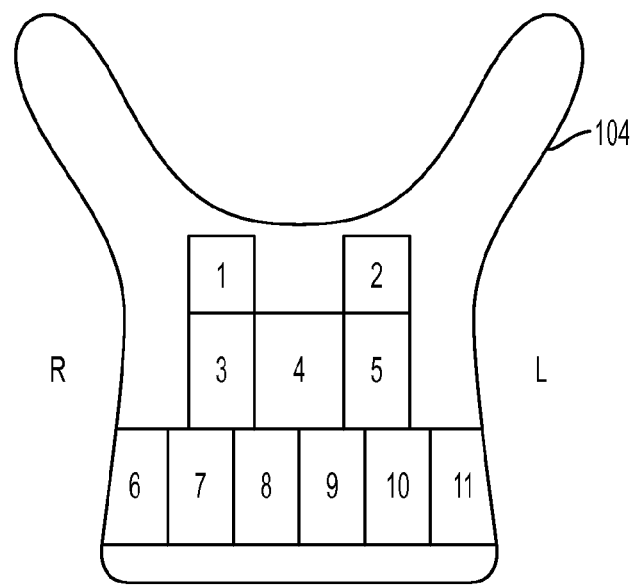
FIGS. 2A and 2B provide front and back panel views, respectively, of an illustrative vest that may serve as a weighted garment or orthotic.
Figure 2B:
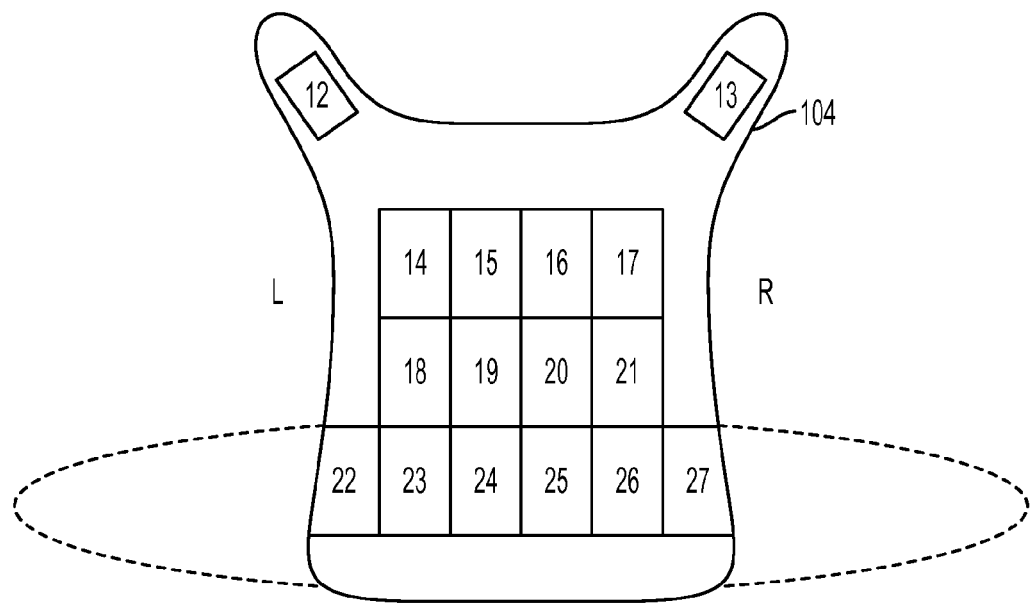

The method of weighting the patient or the orthotic is often dependent on the specific type of patient dysfunction identified during observation step 100 and perturbation testing 116. Reference will now be made to FIGS. 2A and 2B, which show front and back views of one variation of an adjustable balance evaluation tool that is configured as a vest. Again, this vest is a garment that itself may be used either as an end product (i.e., a garment to be worn by the patient) or as a tool to determine the placement and size of weights to be introduced into another garment, perhaps having greater aesthetic appeal. Other test garments may be used in the same way. For instance, it is my intent that test garments having the functional ability to hold a weight in a single position during, for example, perturbation and balance testing, are included as garments suitable as test garments (adjustable balance evaluation tools). For instance, an illustrative garment for testing may comprise, rather than a collection of pockets for inclusion of weights, a tacky exterior or an exterior having Velcro, or another method capable of holding a weight in position. The right side of the vest, while worn by the patient, is indicated with an R. Similarly, the left side of the vest, while worn by the patient, is indicated with an L.

As mentioned above, adjustable balance evaluation tools including those that include pockets or channels for placing weights, typically allow positioning of the weight in any appropriate position across a broad region of the adjustable balance evaluation tool. This may be contrasted with garments including predetermined placement locations for weights. In contrast to the garments described and illustrated herein, these garments may have substantial spacing between locations of the pockets, which would require weights to be positioned securely only in these predetermined locations. For example, in FIGS. 2A and 2B, the adjustable balance evaluation tool is configured as a vest including a plurality of pockets that are immediately adjacent to each other across the surface of the vest (e.g., pocket 19 is immediately adjacent to pockets 14-16, 18, 20, and 23-25). In other variations the entire surface allows for the device to be weighted in any one of an essentially continuous (rather than discrete) locations.

Adjustable balance evaluation tools having pockets therefore do not include substantial (if any) spacing between adjacent pockets, as shown in FIG. 2.

Illustrated below are examples of how a vest may be selectively weighted.

Posterior Balance Dysfunction. To test for appropriate weight placement with this dysfunction, a series of weights from ¼ to ½ pounds may be placed within any of pockets 1-11 until the desired weight shift or perturbation resistance is achieved for adults. In children, the weights may be 1/16, ⅛, ¼, or ½ pounds. Pockets 1-11 are on the front of vest 104. Placement of weight may begin with pocket 4 and continue progressively to pockets 8 and 9 if determined necessary. Directionally, I have found that beginning the testing sequence in the middle of the vest, e.g., pocket 4, progressing downward to pockets 8 and 9, and then to the left and right pockets is a practical progression for this balance disorder. Additional pocket combinations may then be added until the desired weight shift or perturbation resistance is obtained. The desired amount of weight shift or perturbation resistance will be that amount resulting in an acceptable level of improvement in balance or movement from the baseline observation and perturbation steps. Once the desired weight shift or perturbation resistance is obtained, the weight placement (e.g., the amount of weight placed within each pocket and the corresponding weight-pocket location) may be recorded.

Posterior Lateral Balance Dysfunction to the Left. For this malady, a series of weights from ¼ to ½ pounds may be placed within any of pockets 13, 1, 3, 4, 6, 7, or 8 and combinations thereof until the desired weight shift or perturbation resistance is achieved for adults. In children, the weights may be 1/16, ⅛, ¼, or ½ pounds. Directionally, I have found that initially placing the weights higher on the body, and then adding or subtracting them lower on the body, is a practical progression for this malady. The desired amount of weight shift or perturbation resistance will be that amount resulting in an acceptable level of improvement in balance or movement from the baseline observation and perturbation steps. Patients having greater lateral instability than posterior instability occasionally may need a weight placed in a posterior right pocket (e.g., 17, 21, 26, or 27) as well as a weight placed in the front. Once the desired weight shift or perturbation resistance is obtained, the weight placement (e.g., the amount of weight placed within each pocket and the corresponding weight-pocket location) may be recorded.

Posterior Lateral Balance Dysfunction to the Right. To test for appropriate weight placement with this dysfunction, a series of weights may be placed on the anterior left side of the patient with the occasional placement in one pocket in the posterior left side of the patient when the patient has more lateral dysfunction than posterior dysfunction. For example, from ¼ to ½ pounds of weight may be placed within any of pockets 12, 2, 4, 5, 9, 10, or 11, and combinations thereof until the desired weight shift or perturbation resistance is achieved for adults. In children, the weights may be 1/16, ⅛, ¼, or ½ pounds. The desired amount of weight shift or perturbation resistance will be that amount resulting in an acceptable level of improvement in balance and movement from the baseline observation and perturbation steps. Once the desired weight shift or perturbation resistance is obtained, the weight placement (e.g., the amount of weight placed within each pocket and the corresponding weight-pocket location) may be recorded.

Lateral Balance Dysfunction to the Left. I have found that even posterior anterior distribution of weights produces the best result unless the patient has a minor rotation, or decreased resistance or loss of neutral. To test for the appropriate weight placement for this dysfunction then, a series of weights from ¼ to ½ pounds may be placed within any of pockets 13, 1, 3, 6, 7, 8, 20, 21, 25, 26 or 27, and combinations thereof until the desired weight shift or perturbation resistance is achieved for adults. In children, the weights may be 1/16, ⅛, ¼, or ½ pounds. The desired amount of weight shift or perturbation resistance will be that amount resulting in an acceptable level of improvement in balance and movement from the baseline observation and perturbation steps. To provide even weight distribution between the front and back segments of the weighting apparatus, weight may be placed within pockets 3 and 21, or within pocket 6 or 7 counterbalanced by weight placement within pockets 26 and 27 respectively. In some instances it may also be desirable to place a ½ pound weight at the shoulder, for example within pocket 13. Once the desired weight shift or perturbation resistance is obtained, the weight placement (e.g., the amount of weight placed within each pocket and the corresponding weight-pocket location) may be recorded.

Lateral Balance Dysfunction to the Right. To test for the appropriate weight placement for this dysfunction, a series of weights from ¼ to ½ pound of weight may be placed within any of pockets 12, 2, 5, 9, 10, 11, 14, 15, 18, 19, 22, 23, or 24 and combinations thereof until the desired weight shift or perturbation resistance is achieved for adults. In children, the weights may be 1/16, ⅛, ¼, or ½ pounds. These pockets are on the front and back of vest 104. The desired amount of weight shift or perturbation resistance will be that amount resulting in an acceptable level of improvement in balance and movement from the baseline observation and perturbation steps. I have found that beginning weighting on the upper, left, front, side of vest 104, proceeding down the front of the vest, proceeding to weight the upper left side of the back of the vest, and then proceeding down the back of the vest is a practical progression for this dysfunction. In some instances, it may be desirable to provide even weight distribution between the front and back segments of the weighting apparatus. In these instances, weight may be placed within pocket 5 counterbalanced by weight placement within pocket 19. Similarly weight may be placed within pockets 10 or 11 counterbalanced by weight placement within pockets 22 and 23 respectively. In some instances it may also be desirable to place a ½ pound weight at the shoulder, for example within pocket 12. Once the desired weight shift or perturbation resistance is obtained, the weight placement (e.g., the amount of weight placed within each pocket and the corresponding weight-pocket location) may be recorded.

Anterior Balance Dysfunction. To test for the appropriate weight placement for this dysfunction, a series of weights from ¼ to ½ pounds may be placed within any of pockets 15, 16, 19, 20, 23, 24, 25, or 26, and combinations thereof until the desired weight shift or perturbation resistance is achieved for adults. In children, the weights may be 1/16, ⅛, ¼, or ½ pounds. The desired amount of weight shift or perturbation resistance will be that amount resulting in an acceptable level of improvement in balance and movement from the baseline observation and perturbation steps. Pockets 15, 16, 19, 20, 23, 24, 25, and 26 are on the back of vest 104 and a practical progression for weight placement may begin by placing weights on the top portion of the back of the vest and then proceeding downward. In some instances, it may be desirable (e.g., a quicker determination of proper weight placement may be made) to place weights first within one or more of pockets 15, 16, 19, and 20 before placing weights within other pockets, if necessary. Once the proper weight shift or perturbation resistance is obtained, the weight placement (e.g., the amount of weight placed within each pocket and the corresponding weight-pocket location) may be recorded.

Anterior Lateral Dysfunction to the Right. For appropriate weight placement for this dysfunction, a series of weights from ¼ to ½ pounds may be placed within any of pockets 12, 14, 15, 18, 19, 22, 23, or 24, and combinations thereof until the desired weight shift or perturbation resistance is achieved for adults. In children, the weights may be ¹⁄₁₆. ⅛, ¼, or ½ pounds. The desired amount of weight shift or perturbation resistance will be that amount resulting in an acceptable level of improvement in balance and movement from the baseline observation and perturbation steps. Pockets 12, 14, 15, 18, 19, 22, 23, and 24 are on the back of vest 104, and I have found that beginning weight placement in the upper left portion of the back of the vest and proceeding downward, is a practical progression for this dysfunction. In some instances, it may be desirable (e.g., a quicker determination of proper weight placement may be made) if weight placement is first tried within pockets 14 or 18. Once the desired weight shift or perturbation resistance is obtained, the weight placement (e.g., the amount of weight placed within each pocket and the corresponding weight-pocket location) may be recorded.

Anterior Lateral Dysfunction to the Left. To test for the appropriate weight placement for this dysfunction, a series of weights from ¼ to ½ pound of weight may be placed within pockets any of 13, 16, 17, 20, 21, 25, 26, or 27, and combinations thereof until the desired weight shift or perturbation resistance is achieved for adults. In children, the weights may be ¹⁄₁₆. ⅛, ¼, or ½ pounds. The desired amount of weight shift or perturbation resistance will be that amount resulting in an acceptable level of improvement in balance and movement from the baseline observation and perturbation steps. Pockets 13, 16, 17, 20, 21, 25, 26, and 27 are located on the back of vest 104 and I have found that a practical progression for selectively weighting for this dysfunction begins at the top right of the back of the vest and proceeds downward. In some instances it may be desirable (e.g., a quicker determination of proper weight placement may be made) if weight placement is first tried within pockets 17 or 21. Once the desired weight shift or perturbation resistance is obtained, the weight placement (e.g., the amount of weight placed within each pocket and the corresponding weight-pocket location) may be recorded.

Evaluation of proper weight placement may continue as long as necessary to determine whether the patient maintains their COG over their base of support for extended periods. The process to determine proper weight placement is typically iterative and based on trial and observation techniques. That is, after each incremental weight addition, it is often desirable to retest the patient using the perturbation and observation steps described above. In this way, a more accurate assessment of the effect of weight placement on the patient's balance and postural stability may be made.

If treatment is a success 106, then the process of assessing the need for a selectively weighted garment and determining proper weight placement throughout a patient's torso, is at its end 110. As described above, a determination of success is typically based on a comparison of the patient's ability to balance and move before and after the weighting treatment or assessment has begun, and at each step during the weighting process. That is, the patient's improvement is continually monitored from their baseline position (the baseline position being the assessment of the patient after observation step 100 and, optionally, perturbation step 116). The number of treatment trials necessary to reach success is highly variable. For example, the number of treatment trials necessary is often dependent on factors such as, the severity of the dysfunction (e.g., is the dysfunction in only one plane of movement, etc), and the patient's inability to attain or maintain COG over the base of support.

If the treatment is not successful, in that significant further improvement may be had, the treatment may be further checked 108. This typically involves altering the weight placement or overall weight amount. Lighter weights are typically used with smaller, lighter, or weaker individuals. Heavier weights are typically used with larger individuals or those with a greater inability to attain or maintain COG over the base of support. In addition, observation step 100 and perturbation step 116 may be repeated as necessary to further assess the most beneficial weight placement treatment.

When the weighting is successful, the patient's gait may be evaluated in order to assess whether their ambulation, or ability to walk, has improved. The patient may also be asked whether the weight is comfortable to them in order to determine whether any weight adjustments may be necessary. Typically, it is desirable to provide the individual with as little weight as possible while still ensuring that their COG remains over their base of support.

If any further attempt at weight adjustment produces no improvement, the treatment is successful 112, and is at its end 110. If not, there may be a further determination that all treatments have been tried. This typically involves rechecking weight placement and overall weight amount, as well as making use of the perturbation and visual techniques described above. If all selective weighting treatments have been tried, then the selective weighting and the outcome is still unsuccessful, selective weighting may simply be inappropriate for the patient and the assessment process is at its end 110. If not, the selective weighting treatment regimen 104 is begun anew, and repeated.

The above method for determining proper weight placement may be performed manually, with use of a computer, or by some combination of the two. The use of a computer for accepting output signals from a force sensor and for calculating the COG by the subject may be highly desirable. For example, a patient may stand on a support surface or force plate connected to a computer and the computer may receive the patient's output, calculate their current COG, and develop the patient's baseline COG position. One acceptable example of such a system is found in U.S. Pat. No. 5,476,103 to Nahsner filed on Jun. 8, 1993 and entitled, "Apparatus and method for assessment and biofeedback training of leg coordination and strength skills," which is hereby incorporated by reference in its entirety. Other common examples of acceptable computers or processors for use with the present invention are known in the industry.

Figure 3A:
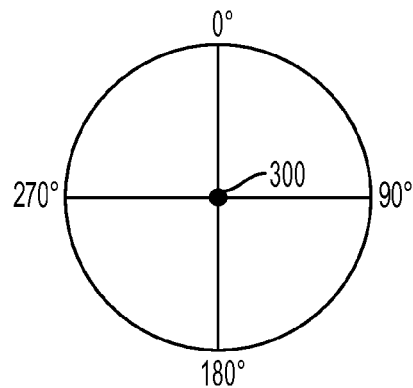
FIGS. 3A through 3C illustrate a computer-assisted weighted method.
Figure 3B:
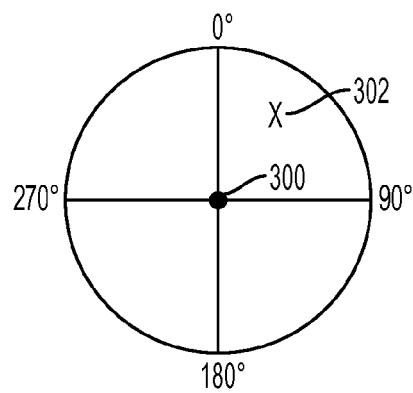
Figure 3C:
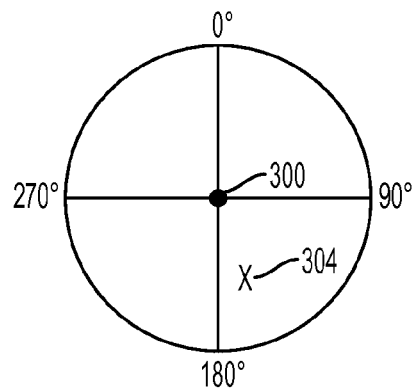

FIGS. 3A through 3C show a procedure for using a computer or processor to measure and facilitate COG correction via proper weight placement. As illustrated in FIG. 3A, position 300 indicates a patient's coordinate system when their COG is aligned over their base of support. FIG. 3B shows one example of a patient's position that is offset from COG as indicated by mark 302. In FIG. 3B, mark 302 indicates that the patient stands anteriorly and laterally (initially at least). Lateral and slight posterior selective weighting may be employed to correct the deficiency and move the patient COG over their base of support.

The procedure described just above i.e., systematically and selectively weighting the orthotic to improve COG placement, may also be employed while the patient is standing on the force plate or support surface. As the amount of the weights and their placement are adjusted, the computer receives the new output and registers the feedback on a screen. Thus, as the patient becomes more centered, mark 302 will move closer to position 300. In this way, the provider will readily be able to determine whether, and to what extent, the weight placement has caused the patient's COG to move toward center. FIG. 3B shows another example of a patient who is off center. In this figure, mark 304 indicates that the patient stands posteriorly and thus the selective weighting procedure may be anteriorly. However, it should be noted that selective weighting does not always begin at a position opposite that of the dysfunction (e.g., weighting anteriorly for a patient who stands posteriorly). These weighting starting points are merely illustrative.

Once a patient has achieved improvement in COG over base of support, or ideally, achieved their optimal COG over base of support, their ability to receive and interpret somatosensory information, coordinate muscular contractions, and move with more stability may then optionally be tested. The use of a computer together with devices for measuring COG, e.g., a plurality of support surfaces or force plates, may greatly facilitate patient assessment and testing in a number of ways. For example, computer assistance may facilitate quicker determination of proper weight placement (e.g., as described above), as well as provide more detailed information regarding a number of different patient positions. These positions may include, but are not limited to sitting, standing (on one or both legs), bending, squatting, walking up stairs. In addition, computer assistance may help provide more detailed information on the patient's reaction while standing on compliant and non-compliant surfaces, such as floors, rugs, etc. In this way, the testing of proper weight placement may be rigorously evaluated while simulating any number of conditions.

My invention also provides weighted orthotics or garments. Proper weight placement and weight size or amount are first determined using the methods described above. Custom garments or orthotics may then be made to accommodate the patient's individual needs. For example, the positioning of the weights and their actual weight values may be recorded using the procedures noted above and mapped onto a garment or orthotic. For example, an adjustable balance evaluation tool (system or device, including the orthotics or garments described) may be used to determine the correct positioning and adjustment of the one or more weights used. Similarly, recordation of the actual weight values may help facilitate a reduction in the overall weight of the garment or orthotic by making use of ratios. Once the location of weights and their values are recorded, tests may be performed to determine if reduction of all or some weight values by a fraction would still produce beneficial results in improving balance. In this way, for example, the amount of each weight may be reduced by a fraction, such as ½, resulting in ½ weight reduction in each location. Ratios may also be used to facilitate a reduction in the size of each weight. For example, the size of each weight may be reduced by a fraction if beneficial results in improving balance are still obtained.

The garments or orthotics (including an adjustable balance evaluation tool) may be of any appropriate form, size, shape, and thickness, in order to accommodate the patient's needs and the therapeutic weighting described herein. For example, the orthotic may take the form of a weighted shoulder pad, a weighted belt, a weighted seating device to be used in combination with a wheelchair, e.g., a weighted vest or other garment that may be attached (e.g., using Velcro or magnets) to the back of a wheelchair seat to improve the patient's stability, a weighted attachment to a brassiere, a brace configured to fit a patient's torso, head, or body part, or any other weighted orthotic. Similarly, the weighted garment may be a brassiere, tee shirt, body suit, belt, hat, headband, eyewear, shoe, glove, jacket, pants, cape, vest, or any other garment to be worn. For example, desirable garments may be those specifically designed as undergarments, e.g., those typically worn substantially out of public view (depending of course, on taste) or intended to be worn underneath outer garments, such as shirts, blouses, and jackets. One variation specifically includes the undershirts, brassieres, girdles, or girdle-like garments mentioned elsewhere. Of course, such undergarments may be made of fabric that is comfortable against the skin. The garment may be self-fastenable (using, e.g., buttons, snaps, hook and latch fabric, such as Velcro, and magnets, etc.) or held to the torso using belts, bands, etc.

The weights for placement within any of the weighted apparatuses may be rigid or may be flexible. The weights may be made of any suitable material, and be able to accommodate any thickness. When the weighted apparatus is a body suit or brassiere, for example, the weighted material may be flexible, thin, and made of a hypoallergenic material. In this way the entire suit or brassiere may be made of the weighted material, having a weight distribution determined in accordance with the above methods. In other variations, the material itself may not be weighted, but may incorporate weights therein. Any suitable type of weight may be used. For example, in one variation, flexible weights are used, of the type described in U.S. Pat. No. 6,005,041 to Cook filed on Nov. 9, 1995 and entitled "Reinforced Thermoplastic Elastomeric Gel (RTEG)," which is hereby incorporated by reference in its entirety.

In other variations, the weights are provided in packets having at least one hook and latch fabric, magnetic, or other easily attachable surface or portion. Thus, the weights may be inserted into a weight packet that is attachable to the garment (e.g., the adjustable balance evaluation tool). In this way, the weights themselves may be attached to the apparel of the patient. For example, the weight packets may be attached to the waistline of a pair of paints, or may be attachable to a portion of a shirt, jacket, belt, etc. Thus, different weights may be loaded into a standard-size weight packet. In some variations, the weight packets may include one or more pockets for inserting one or more weights (allowing adjustment of the weight at a location by adding to the weight packet. One or both sides of the weight packets may include a fastener (e.g., snap, hook, etc.) or adhesive material (chemical adhesive, mechanical adhesive such as hook-and-latch (i.e., Velcro) material, etc.), or the like, to secure it to the garment. In some variations the weights themselves are configured to attach to the adjustable balance evaluation tool or garment. For example, the weight may include a fastener (e.g., snap, hook, etc.) or adhesive material (chemical adhesive, mechanical adhesive such as hook-and-latch (i.e., Velcro) material, etc.), or the like.

I have found an adjustable balance evaluation tool configured as a weighted vest to be especially useful. The vest may have any number of optional panels, but typically may have a pair of front panels separated by a front, closing seam and a back panel or of course, it may be made up of: a front panel, a back panel, or side panels. The vest may be made of any number of suitable materials. The vest may be made of durable materials capable of withstanding the weight therein and capable of maintaining its integrity in the event the wearer falls. The vest may have a continuously adhesive surface (e.g., a Velcro-type, hook-and-loop surface for receiving a weight or weight packet) and/or may have any number of pockets or receptacles for receiving and securing the weights therein, as described above. Alternatively, the vest may have no pockets or receptacles and be manufactured in accordance with the above methods, wherein predetermination of the proper weight distribution is made and the material of the vest is weighted in accordance therewith. For example, the vest may be made so that the weight is permanently affixed and is not readily adjustable after fabrication, based on the determination of the weight location and amount made above. In general, such garments (customized and non-adjustable balance correcting garments) include one or more weights that are positioned in locations that are non-symmetrical relative to the body, but are therapeutically positioned to correct or assist the balance for the individual for whom the garment is customized. The weight is typically between about 0.05% to less than 3% (e.g., less than 2%, around 1.5%) of the subject's body weight. In some variations only a single weight is used, and is secured on an asymmetric position on the garment (relative to the subject's bilaterally symmetry—front/back and right/left symmetry).

The vest may be of any length and shape to accommodate the wearer's height, size, body type, comfort, and ability to maneuver about while wearing it. Similarly, the vest may be of any thickness so that it may be worn in any number of ways. For example, in one variation, the vest is relatively thin so that it may be worn underneath the wearer's clothing. In other variations, the vest is thick and may be worn on top of the wearer's clothing.

Figure 4A:
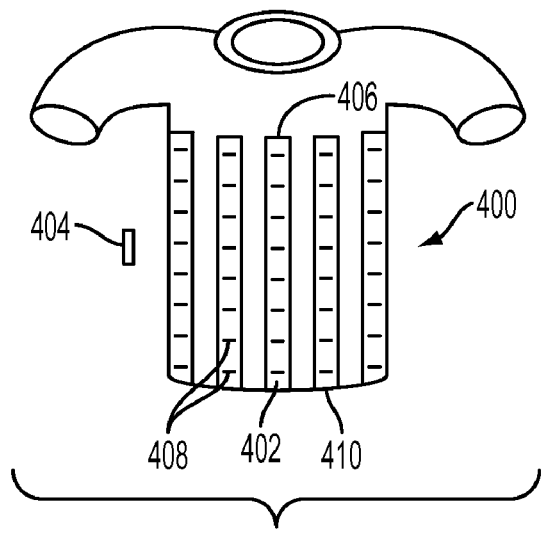
FIGS. 4A through 4C show a weighted shirt having longitudinal tubes for the introduction of weights.

Another weightable or weighted garment of particular usefulness is shown in FIG. 4A. The garment 400, although shown in the form of a shirt, may be a vest, corset, or other apparel, having at least a portion worn on the torso. Central to this garment 400 are the linear enclosures 402 that are adapted to receive weights in shapes and forms that may be inserted into the linear enclosures 402. Shown in FIG. 4A are linear enclosures 402 having an open upper end 406, cross-slits 408, and open lower end 410. Each of the linear enclosures 402 would typically have the openings specified just above.

Figure 4B:
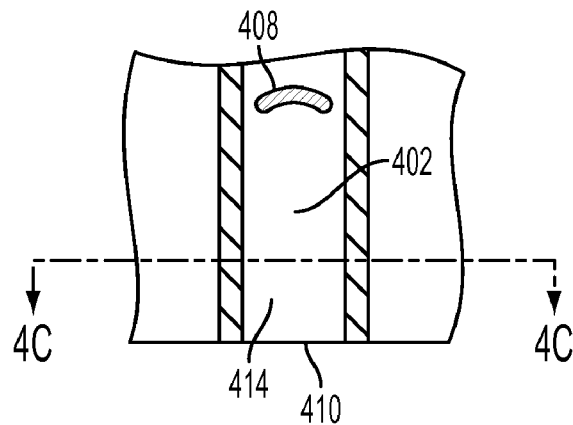
Figure 4C:
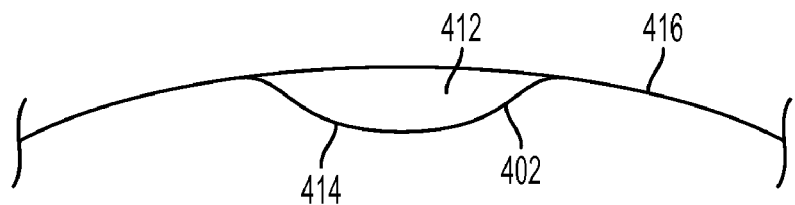

FIG. 4B shows a partial close-up view of one of the linear enclosures 402 with the open cross-slit 408 and the open bottom end 410. FIG. 4C shows a top view cutaway of a linear enclosure 402 and the open space 412 within for placement of an appropriate weight. The linear enclosure 402 shown in FIGS. 4B and 4C is made up of a cover 414 that is surged to the backing material 416.

I have found that constructing one or more of the cover 414 and the backing material 416 from a stretchable material such as nylon, Lycra®, or the like, tends to hold the weights in position in the linear enclosures, particularly if the weights are resistant to movement after placement or covered with a rubber material. Returning to FIG. 4A, the linear enclosures 402 shown there are positioned longitudinally with the torso of the wearer. However, they need not be so. Other configurations, helical about the torso, of differing widths, as well as single enclosures having varying widths, are also suitable.

Figure 5A:
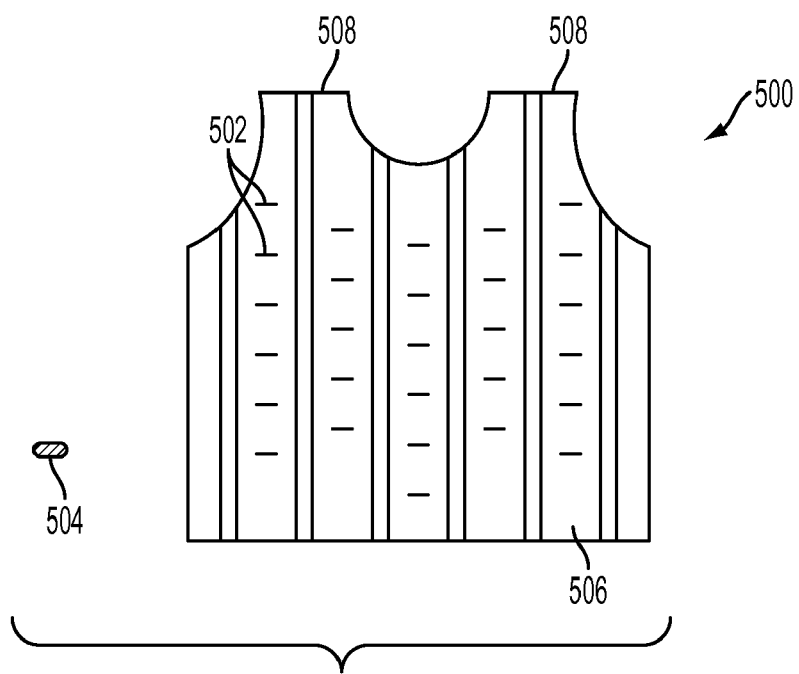
FIGS. 5A and 5B illustrate garments having slits for the introduction of weights.
Figure 5B:
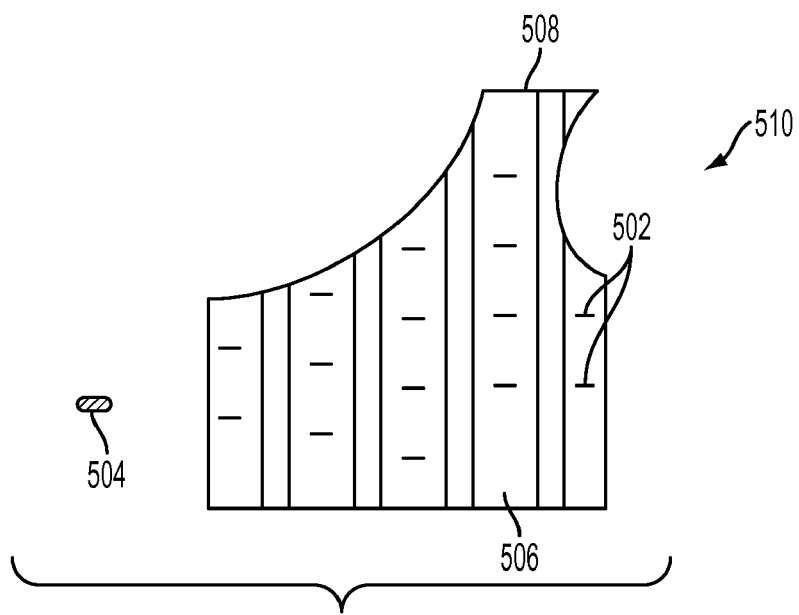
Figure 5C:
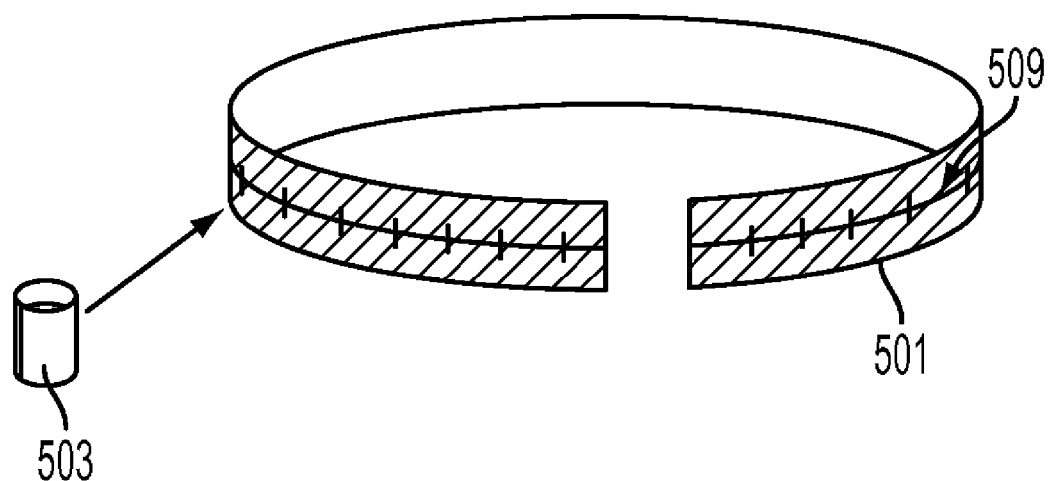
FIG. 5C illustrates a garment configured as a belt showing a weight packet that may secured thereto.

Other useful weighted garments are illustrated in FIGS. 5A and 5B. FIG. 5A illustrates a weighted garment 500 configured to be worn about both shoulders while FIG. 5B illustrates a weighted garment 510 configured to be worn about one shoulder. The garments 500 and 510 may be double layered for example, and be made of a breathable and stretchable material. Slits 502 are provided variously along the length of the garments for the introduction of weights 504. Slits for weights may also be provided on the shoulder portions of the garments 508. The weights 504 may be held in place, for example, by sewing the weights in place at or near slit 502 or the weights may be allowed to migrate to the base of the garment 506 before being sewn in place. In addition, any of the methods of attachment described above (e.g., hook and latch fabric, magnetism, etc.) may be employed here. In addition, while horizontal slits are represented here, the slits need not be so. Other configurations are also suitable. For example, FIG. 5C is another variation of an orthotic device configured as a belt, as described above. A weighted packet 503 may be positioned and secured to the inner, outer, or either side surface of the device 501 by any of the attachment mechanisms described. The orthotic device shown in FIG. 5C also illustrates markings 501 uniquely indicating the position of any attached weight packet 503, as described above.

As mentioned above, the adjustable balance evaluation tools described herein may also be referred to as orthotics or garments. These devices (which may also be systems including multiple components, as described below) may be used during the testing/analysis portion of the method to determine where to position one or more weights. After determining where the weight or weight should be positioned, a separate (e.g., customized, non-adjustable) garment or orthotic may be made using the information taken from the adjustable balance evaluation tool. Thus, described herein is a method for creating a customized orthotic that may include the steps of using an adjustable balance evaluation tool to determine the position and weight appropriate to benefit a patient, as described above, then securing a corresponding weight to a customizable garment in the position identified. Any appropriate garment may be used. The weight may be permanently secured (e.g., sewn to the fabric or within the garment), or it may be temporarily secured. In some variations a pocket or attachment site is positioned on the garment at the appropriate (custom, patient-specific) site so that the weight may be attached/detached by the user. As mentioned, more than one site may be used. Variations including attachment sites that are positioned by this method may be configured for use with 'weights' that are devices or objects weighing the same or less than described that are not simply therapeutic weights but achieve improved balance. For example, the 'weight' that may be attached to the custom garment may be a cold or hot pack, cell phone, sensor, or other device. The attachment site may be a pocket or region including a fastener (or for mating to a fastener). In practice, the attachment site(s) for any particular patient are specific to that patient, and each garment may have one or more weights or attachment sites for weights at these specific sites. A custom garment may include one or more weights (or an attachment site for a weight) that is typically positioned on a discrete location (e.g., smaller than 4∴4 inches) in an asymmetric position on the garment. For a garment worn on the torso, the weight or attachment site may be located on the back, front, shoulders, or sides.

In some variations, the adjustable balance evaluation tool may be used, or adapted for use, as a customized garment or orthotic. For example, once positioned, the weight may be permanently attached to the adjustable balance evaluation tool (making it non-adjustable), or it may be attached to, or within, a portion of another garment. For example, the adjustable balance evaluation tool may be coupled with a garment such as a shirt, vest, bra, jacket, or the like. Examples of adjustable balance evaluation tools adapted to be customized garments or orthotics are provided in detail below (e.g., FIGS. 13A-20).

Figure 7A:
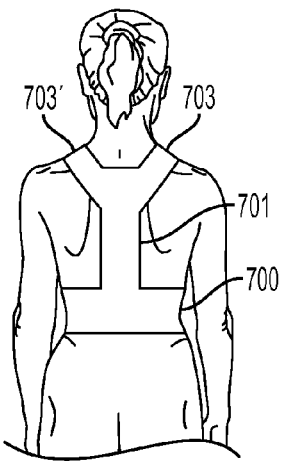
FIGS. 7A-7E show variations of an adjustable balance evaluation tool (garment) which includes two or more straps and a waist point.
Figure 7B:
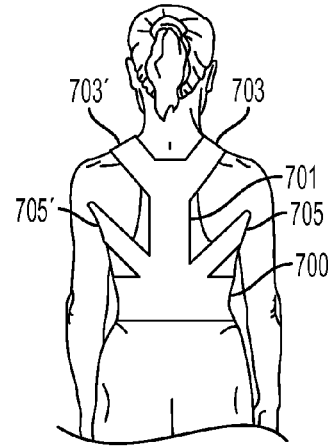
Figure 7C:
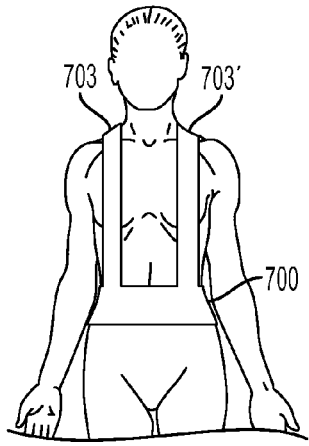
Figure 7D:
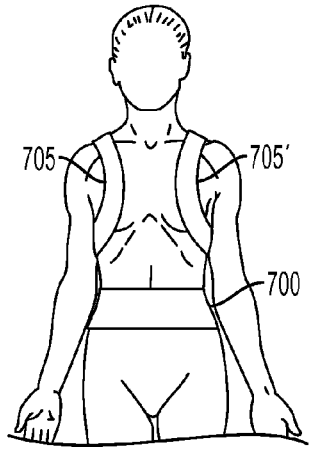
Figure 7E:
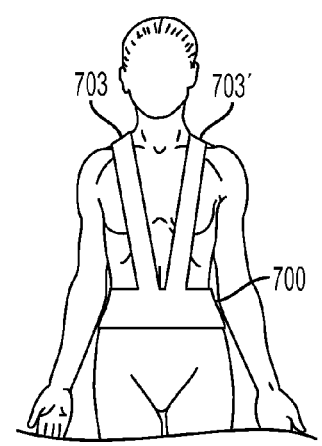

FIGS. 7A to 7E show different variations of adjustable balance evaluation tools or systems as described herein. For example, FIGS. 7A and 7B show back views of two variations of adjustable balance evaluation tools. In FIG. 7A, the adjustable balance evaluation device includes a back strap 701 that connect to a belt region 700. The back strap 701 also connects (or is continuous with) two shoulder straps 703, 703', one for each shoulder. The shoulder straps can then pass over the front of the torso, as illustrated in FIGS. 7C and 7E, and connect to the belt region 700 on the front of the garment. The straps and belt may be different components that mate with each other, or they may be formed as a single garment. The variation shown in FIG. 7B includes lateral straps 705, 705' that pass under the arms and over the shoulders, as illustrated in FIG. 7D. The configuration of the adjustable balance evaluation tool may depend on the patient. In particular, the configuration may depend on the anticipated needs of the patient based on where it is anticipated that weights will be placed, as described in the methods above. In some patients more lateral placement of weights is necessary, thus the configuration shown in FIGS. 7B and 7D may be more appropriate.

In all of the variations shown in FIGS. 7A-7E, the straps and belt portions typically include one or more axis of markings, indicating where on the adjustable balance evaluation tool (relative to the patient's body) the weight or weights are placed during treatment. For example, a ruler or calibrated pattern may be formed on the straps and/or belt. The entire adjustable balance evaluation tool may be configured to allow attachment of a weight or weights. For example, one surface of the adjustable balance evaluation tool (the inner or outer surface) may be configured to allow a weight to be secured thereto. For example, the outer surface may be a Velcro material that is configured to mate with a Velcro hook material on the weight or weight packet. The markings along the adjustable balance evaluation tool indicating the position of the weight may be on the same side or the opposite side of the garment (inside or outside).

As mentioned, the adjustable balance evaluation tool may actually be an adjustable balance evaluation system, including a plurality of connecting straps that are adapted to attach to one or more weights or weighted packets, and include calibration marking uniquely identifying the position on the straps where the weight is positioned relative to the patient's body. The system may include one or more weights, which may be directly attachable to the straps, or they may be used with one or more weight packets that are attachable to the straps.

Figure 8A:
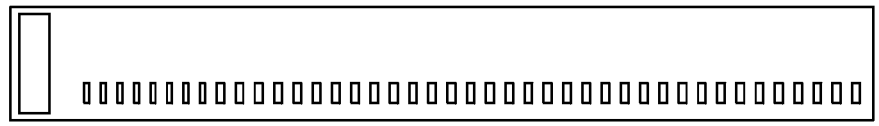
FIGS. 8A and 8B show the front and back, respectively, of one variation of a belt for use as (or as part of) an adjustable balance evaluation tool.
Figure 8B:

For example, FIGS. 8A-8B and 8C-8D show two components of an adjustable balance evaluation system. FIGS. 8A and 8B show the calibrated inside and solid outside, respectively, of a belt such as the belts illustrated in FIGS. 7A-7E. The belt may include one or more surfaces that are configured to secure a weight or weights. For example, the belt may have a surface that is made of a Velcro material configured to mate with a Velcro hook material. The belt is typically adjustable so that it can fit a variety or range of waist sizes, and may be secured in place using a buckle, latch, or other material such as a Velcro attachment between the end regions. In FIG. 8A, the inside surface of the belt includes indicators (a numbering system that can be used on other portions of the device to indicate position). FIG. 8B shows an outside surface of the device of FIG. 8A. In this example, the outside surface is adapted to secure a weight thereto, e.g., via Velcro. Thus, the outside surface includes a Velcro receivable surface, allowing the weight to be positioned anywhere on the surface of the device in a non-predetermined manner. In other variations the outer surface is configured to secure a weight or weights by a zipper, stay, track, button, magnet, or other means.

Figure 8C:
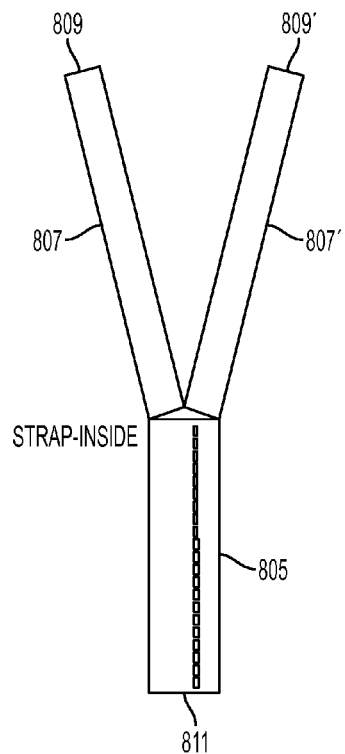
FIGS. 8C and 8D show the front and back, respectively, of a torso strap portion of an adjustable balance evaluation tool, which may be used in conjunction with the belt portion shown in FIGS. 8A-8B.
Figure 8D:
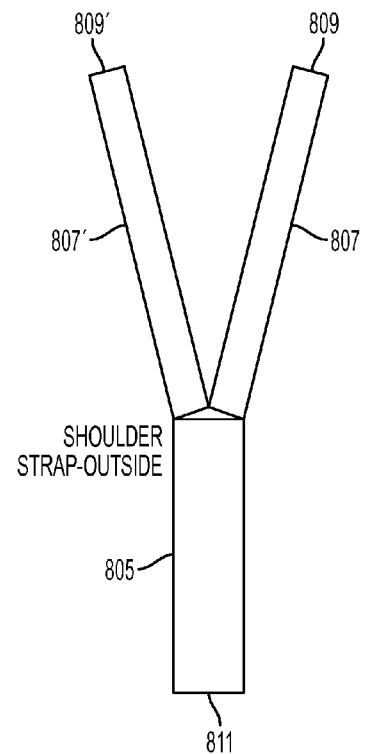

FIGS. 8C and 8D illustrate one variation of straps which may be part of an adjustable balance evaluation system. In this example the straps may also include a numbering system as illustrated for the belt (FIG. 8A), and one or more surfaces (e.g., the outer or inner surfaces) may be configured to secure a weight or weights (either directly or via a weight packet). The straps in this example, include a back portion 805 and two over-the-shoulder portions 807, 807'.

The straps shown in FIGS. 8C and 8D are configured to connect to the belt of FIGS. 8A and 8B. Thus, the ends of the straps 809, 809', 811 may be coupled securely to the belt. In general, an adjustable balance evaluation tool may be customizable to fit the torso of an individual by adjusting the length of the straps. For example, the ends may be cut or otherwise shortened and connected to a connector to couple to the belt. FIGS. 8H-8J illustrate variations of connectors that may be included as part of an adjustable balance evaluation system. A connector may be secured to the end 809, 809', 811 of a strap. For example, the connector may be folded over the cut end of the strap (after it has been cut to fit the subject), and locked over the strap by a connector (e.g., fastener), adhesive (Velcro, chemical adhesive, etc.), sewn, or otherwise secured. The connector may be a Mila clip, allowing for customizing of the length of the straps, and securing them to the belt. The connector may include a hole or opening through which the belt is threaded, or it may include a fastener. In FIGS. 8I and 8J, the connector includes an outer surface that is a Velcro material that can mate with the Velcro receiver on the belt (or vice-versa).

FIG. 8E illustrates one variation of a weight packet 820 including a pocket 822 into which a weight (e.g., the weight shown in FIG. 8F) may be positioned. The weight packet may also include one or more sides configured to couple to the adjustable balance evaluation tool, such as a fastener or Velcro-hook material. The weight packet may be used with weights of a variety of sizes, widths, and weights. More than one weight may be inserted or held by a weighted packet. FIG. 8G is one variation of a weight that includes a fastener on one side (e.g., a Velcro hook material). Other fasteners may include buttons, snaps, magnets, Velcro, adhesives (e.g., glues), zippers, etc.

As mentioned above, any appropriate weight may be used. For example, the weight may be a mass formed of a metal or other dense material (e.g., lead, steel, etc.), a gel material, sand, reinforced thermoplastic gels, magnets, pellets, rubber, liquids (e.g., water), etc. In some variations the weights are calibrated to be of known weight (e.g., ¼ pound, ½ pound, etc.), and may be marked. The weights may be (or may include) magnets for magnetically attaching to the adjustable balance evaluation tool. In some variations the weight is an active element such as an electrical stimulation device, thermal device, or a vibration device, which may provide additional therapy or therapeutic benefit when worn. In some variations the weight is an element that is configured to perform an additional or separate function. For example, the weight may be a cell phone or other (normally) handheld device. The weight may be a wallet or pouch which may hold additional material. In still other variations, a patient's sensory system can be stimulated by compression. In such variations, the stimulus stimulates a person's sensory system by compressing a portion of the patient's body. Such compression stimulus can be provided by any of the apparatuses and garments described herein. Compression can be provided on any body part including, but not limited to, a patient's head, neck, arm, wrist, shoulder, torso, back, waist, leg, hip, foot, etc. The compression can be provided by adjustable bands or elastic material at desired locations.

In some variations, the 'weight' may be a device such as a sensor or console for a sensor. For example, a controller or console (e.g., Wii game controller) including motion and/or position sensor may be used as a weight or in place of a weight. This may allow tracking or recording of the COG movement interactively.

The adjustable balance evaluation tools and systems described herein may be used as indicated to help assess and determine how to treat a balance disorder. In addition to providing weight as indicated above, these systems and devices may also be used to provide additional sensory treatment modalities such as vibration, electrical simulation, or the like. The weight typically imparts a non-symmetrical force to the subject through the garment (based on its position) to help stabilize the patient in need thereof. In general, adjustable balance evaluation tools such as those described herein (which may be customized to fit and measure each subject specifically) may provide many benefits. Since the device may be customized and adjusted continuously, the treatment may be optimized. The clinician may use the device to assess the effects of the treatment. Also, as mentioned above, an adjustable system or device such as those described herein may be used to create customized non-adjustable garments or orthotics.

Any of the adjustable balance evaluation devices and systems described herein may be fully adjustable. Thus, these devices may be adjusted to fit multiple body sizes, from tall to short, large to thin, or the like. As described for FIGS. 8A-8D, the straps and belt in some variations may be adjusted to fit different torso sizes, and the resulting device is easy to apply, and may be lightweight and fit snugly. In addition, variations comprising one or more straps may be comfortably worn, since they cover only a portion of the patient's body, and do not bind the patient's movements, although they may provide stability in multiple planes of movement. In addition, these devices and systems may be quickly applied (and customized) and may be worn by the patient over a long time (e.g., minutes, hours and even days). These adjustable balance evaluation tools may be non-obtrusively worn beneath other clothing, or over other clothing, as mentioned.

In operation, a device such as the one shown in FIGS. 8A-8D may be fit to a subject by placing the straps onto the back and shoulders of the subject, attaching the belt around the waist of the subject, measuring and cutting the front straps, attaching the clips (connectors) to the ends of the straps, attaching the straps to the belt, and then placing the weights as described above.

In some variations the adjustable balance evaluation tool includes just a belt, without the upper torso straps or vest region. For example, an adjustable balance evaluation system may include a belt as shown in FIGS. 8A-8B.

Figure 9A:
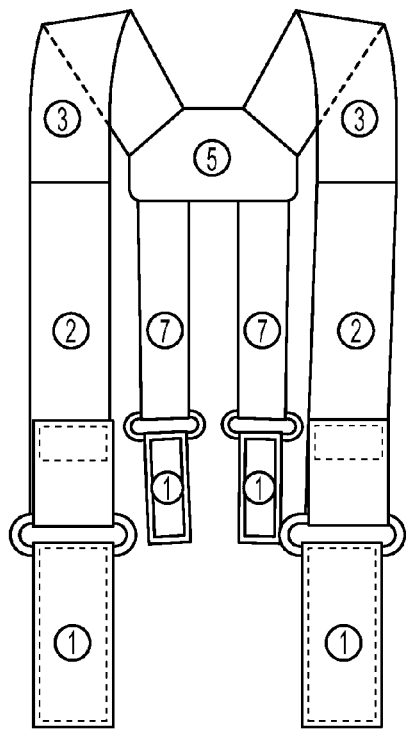
FIGS. 9A and 9B show front and back views, respectively, of a portion another variation of an adjustable balance evaluation tool.
Figure 9B:
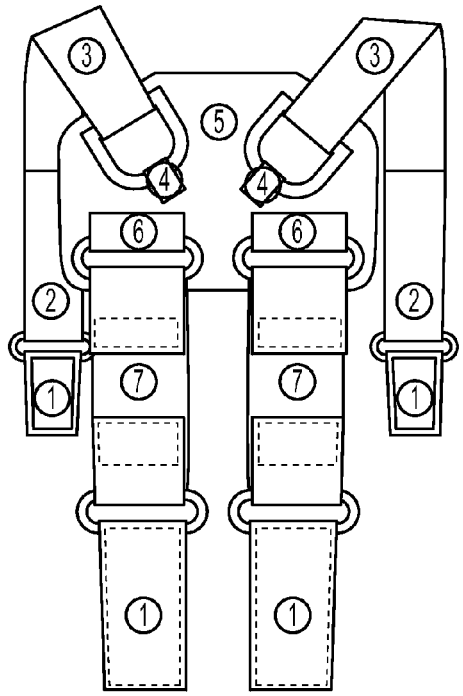

FIGS. 9A and 9B illustrate another variation of an adjustable balance evaluation system. The device shown in FIGS. 9A and 9B is configured as an adjustable "suspender" orthotic. This variation may be attached to a belt (e.g., the belt shown in FIGS. 8A-8B) around the patient's waist. The belt may be made of a stretchable material, and may include a receiving surface for receiving a Velcro-type hook on both inside and/or outside of the belt. The suspenders shown in FIGS. 9A and 9B are fully adjustable in height in both front and back for proper patient fit. A weight or weights may be placed anywhere along the straps (or belt, in some variations). For example, the weight may include a Velcro or Velcro-type hook material (or be secured in a weight packet with a fastener such as Velcro hook) and placed anywhere on the suspender's straps.

In FIG. 9A, all or a portion of the straps may be made from a Zloop or other Velcro-type receivable material, particularly on the outside of the device. The ends of the straps (region marked "1") may include Velcro-hook type material to secure to the belt, or other clip-on suspender hardware may be used to attach the straps to the belt. The region marked "2" may also be made of a Velcro-type receivable material on both sides with a Velcro-hook type material on the ends, allowing adjustment of the length by folding this region back on itself after passing through the loop, as shown. The region marked "3" may be made of a stretchable Velcro-type receiving material that is attached to D-rings on the back (shown in FIG. 9B). The strap could also be made to thread through the D-ring and attach back to itself to allow more adjustment. The D-rings on the back may be pivotable to allow adjustment of the shoulder region. The back of the device (region "5") make also be made of a Velcro-type receiving material. The lower back region ("7" and "8") are also made of an adjustable Velcro-type receiving material (and a region of Velcro-type hook material) and can be adjusted to the subject's height before attaching to the belt, as described.

Figure 10A:
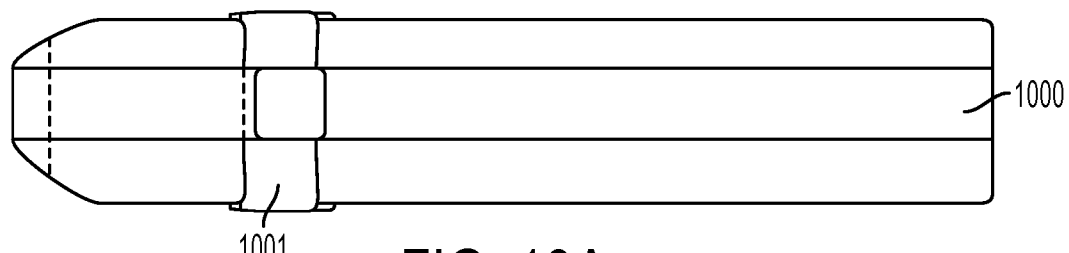
FIG. 10A shows one variations of portion of an adjustable balance evaluation tool, which may form part of a strap or belt.
Figure 10B:
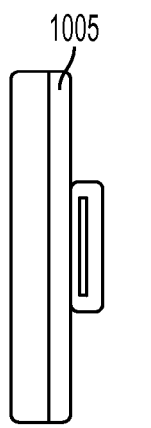
FIGS. 10B and 10C show side and back perspective views, respectively, of an adjustable-position weight for use with the tool shown in FIG. 10A.
Figure 10C:
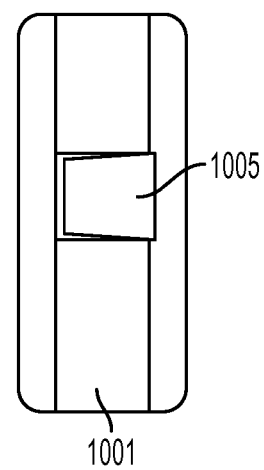
Figure 10D:
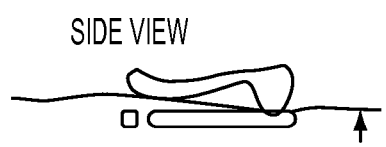
FIG. 10D illustrates a clasp mechanism for use with the tool shown in FIG. 10A.

The example, shown above includes straps (shoulder straps) and a belt, and the weight or weights are attached in any (non-predetermined) position using a Velcro-type attachment. FIGS. 10A-10D illustrate another variation in which the weight or weights are attached to a track or strand on the strap(s). For example, FIG. 10A shows a region of a strap (or belt) 1000 that includes a central fastener track 1001 to which one or more weights may be attached (either directly or via a weight packet). FIGS. 10B and 10C illustrate a weight including a coupling or fastening region 1005 that attaches to the central fastener track 1001 so that the weight is held in place. In this example, the coupling region is a clip-like structure that allows the weight to be secured under the central fastener track 1001 after it has been clipped on. In some variations the weight may be slid along the fastener track 1001 to adjust the position of the weight. For example, FIG. 10D shows a partial side view through a fastener including a friction clip that may be released (e.g., by pushing on one end of a release lever) and allowed to slide on the central fastener track or removed from the track entirely. In some variations the device also includes markings on either the central fastener track or the strap 1000, or both.

Figure 11A:
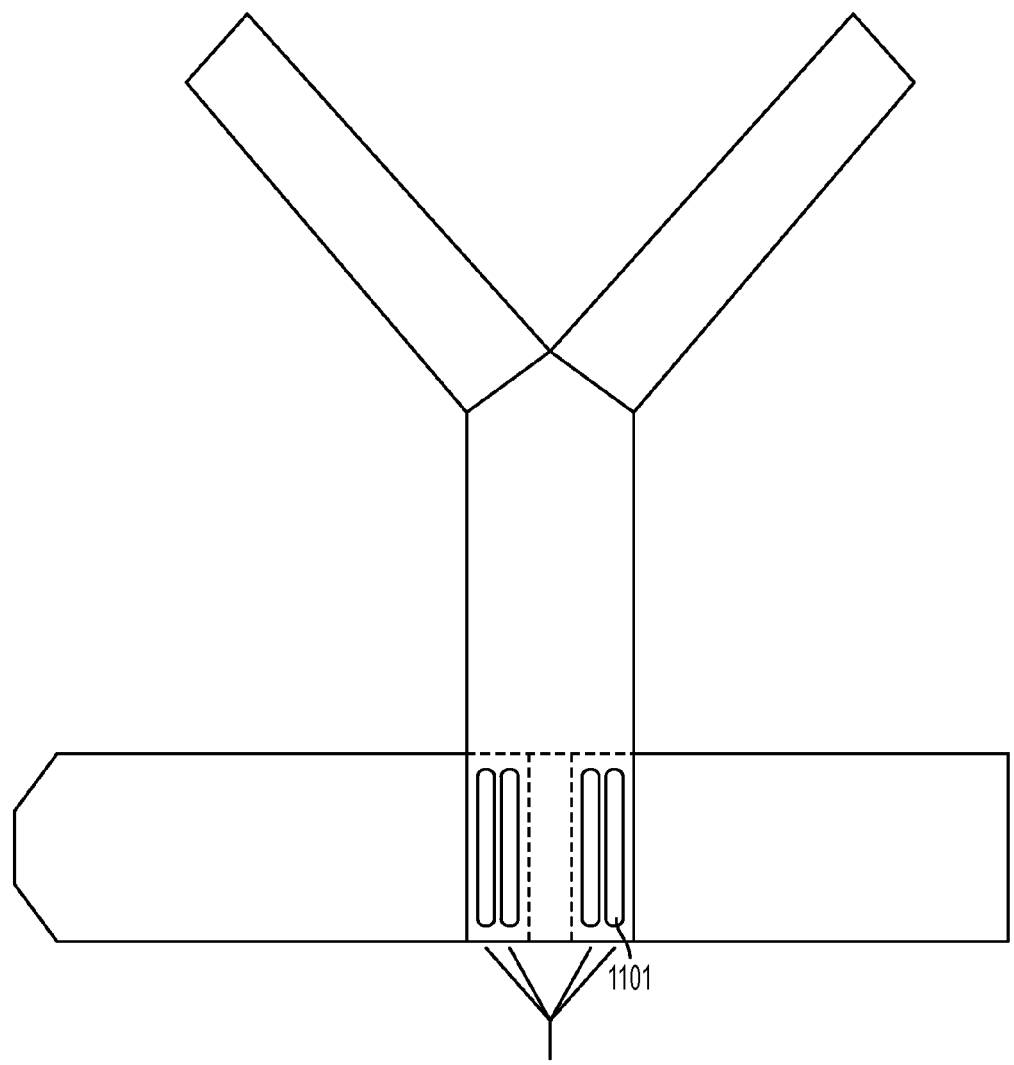
FIG. 11A shows one variation of an adjustable balance evaluation tool, including a support region.

FIG. 11A shows another variation of an adjustable balance evaluation system in which the belt and the straps (e.g., shoulder straps) are connected prior to being applied to the subject. In this variation, the back of the device (particularly the region near the belt) may include one or more flexible or non-flexible stays 1101 of any appropriate size or length (e.g., the stays may be as long go up the garment to the upper thoracic area, or longer) within or attached to the device to provide increased support to the device. The back strap region may also be adjustable (not shown), and the front straps may be adjustable as well, allowing the device to be custom-fit to different body shapes and sizes. For example, the front straps may be cut and the ends attached to a connector (e.g., clip) for attachment to the front of the belt.

Figure 11B:
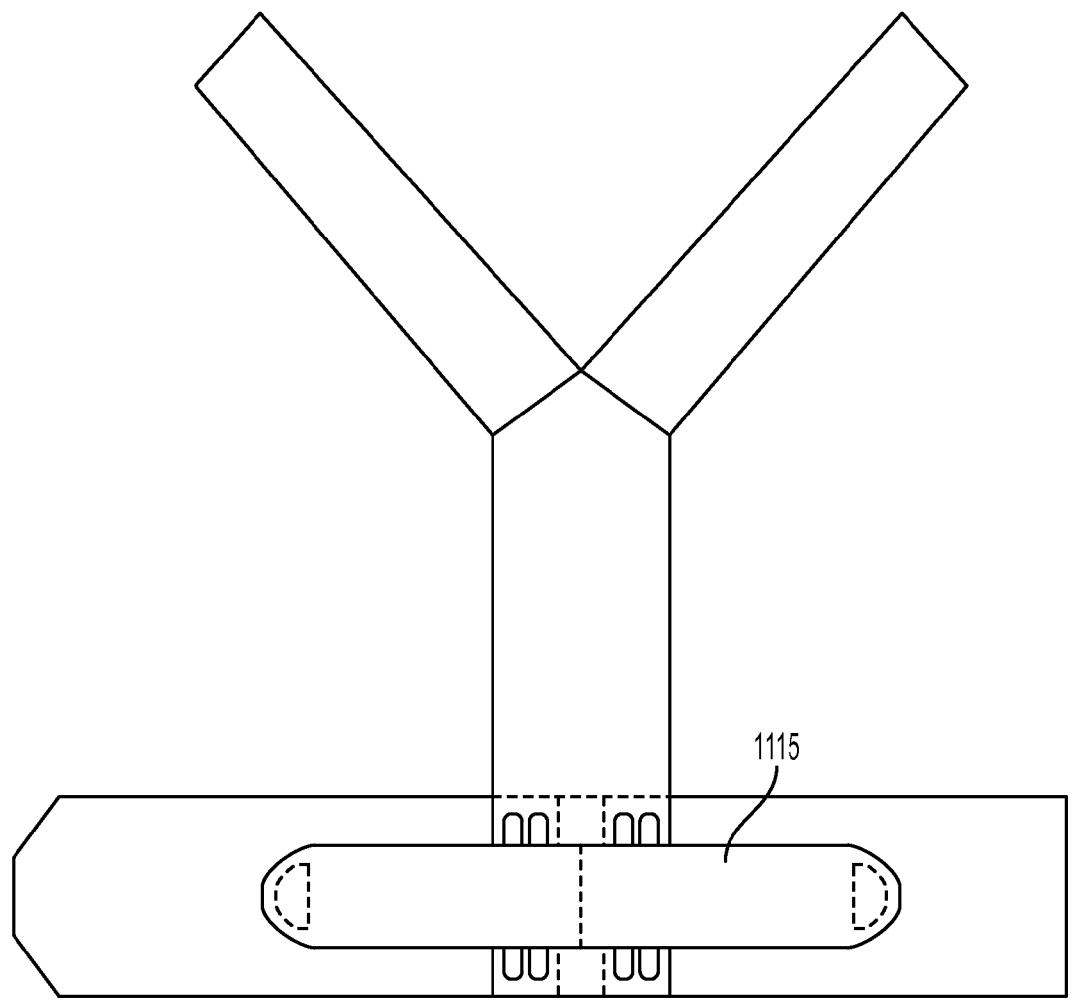
FIG. 11B shows another variation of an adjustable balance evaluation tool similar to the variation shown in FIG. 11A.

FIG. 11B shows an alternative variation, in which a compression strap 1115 (which may be removable) may be attached to the back of the belt, providing additional support to the wearer. Compression strap 1115 may be elastic and may be sewn to the side of the belt. The outward-facing side of the compression strap may also be configured to allow connection of a weight (e.g., having a Velcro-type receiving surface). FIG. 11B also includes four flexible stays that may be sewn into the belt.

Figure 12A:
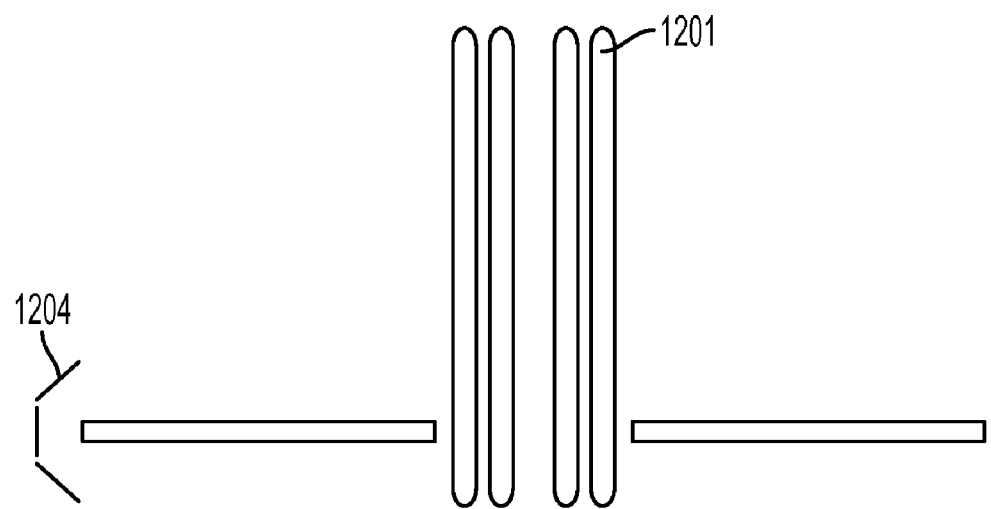
FIG. 12A shows a schematic of a support region for use with an adjustable balance evaluation tool.
Figure 12B:
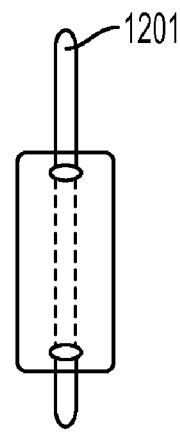
FIG. 12B shows one variation of an adjustable-position weight for use with the tool shown in FIG. 12A.

FIG. 12A shows another variation of an adjustable balance evaluation system, in which stiffening or support members 1201 are included along the straps forming the device, and may also be present along the belt 1204. These support members 1201 may be stiffening members, and may be formed of any appropriate material. In some variations the stiffening members are wire or other material secured to the strap(s) and/or belt. In some variations the stiffening material may provide an attachment site for the weights or weight packets. FIG. 12B illustrates one variation in which the stiffening member 1201 forms a track for the weight to be secured to (similar to the embodiment shown in FIGS. 10A-10D). In some variations the weight or weight packet is threaded over the track-like member on the garment.

FIGS. 13A-25 illustrate various embodiments of garments configured as adjustable balance evaluation systems or devices. In many of these variations the adjustable balance evaluation system is incorporated or integrated with a garment such as a jacket, shirt, pant, skirt, or the like. The adjustable balance evaluation system may be adapted for long-term use by securing the weight in position more permanently after it has been positioned, or it may remain adjustable. In some variations the garment includes a shell or other portion that connects (either permanently or removably) to the adjustable balance evaluation system, including adjustable balance evaluation systems such as those described above (e.g., FIG. 7A-7E).

Figure 13A:
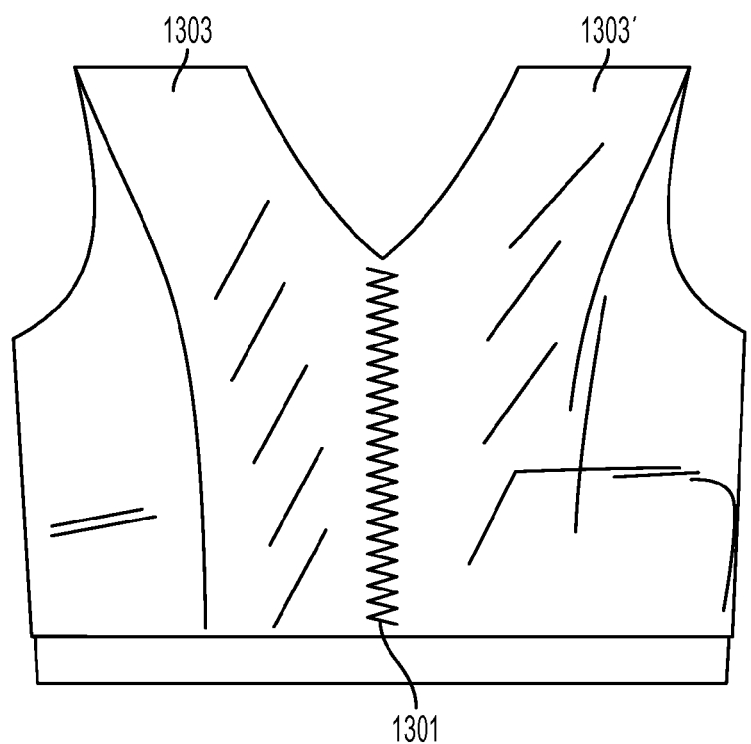
FIGS. 13A and 13B show front and back views, respectively, of an adjustable balance evaluation tool configured as a bra.
Figure 13B:
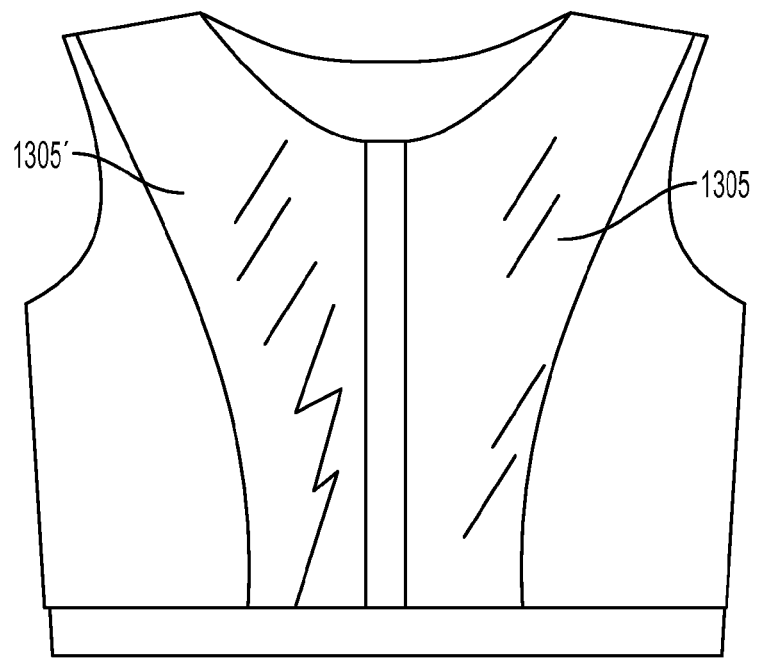

For example, FIG. 13A shows an adjustable balance evaluation system configured as a bra, including a sports bra. In this example, the adjustable balance evaluation system may include a fused elastic stretch material that has an internal material for securing a weight, such as a Velcro-type material, a tacky surface, adjacent pockets, or the like. FIG. 13A shows the front of the athletic or sports bra. The mid-region of the garment includes a central zipper 1301, and adjacent to this region an attachment region 1303, 1303' to which one or more weights may be attached. The back of the device is shown in FIG. 13B. The back (like the front) in this example, includes panels 1305, 1305' of Velcro receivable material fused to an elastic material allowing the placement of a weight across the back region in a non-predetermined manner. The garment may also be marked to uniquely indicate where a weight has been placed.

Figure 14A:
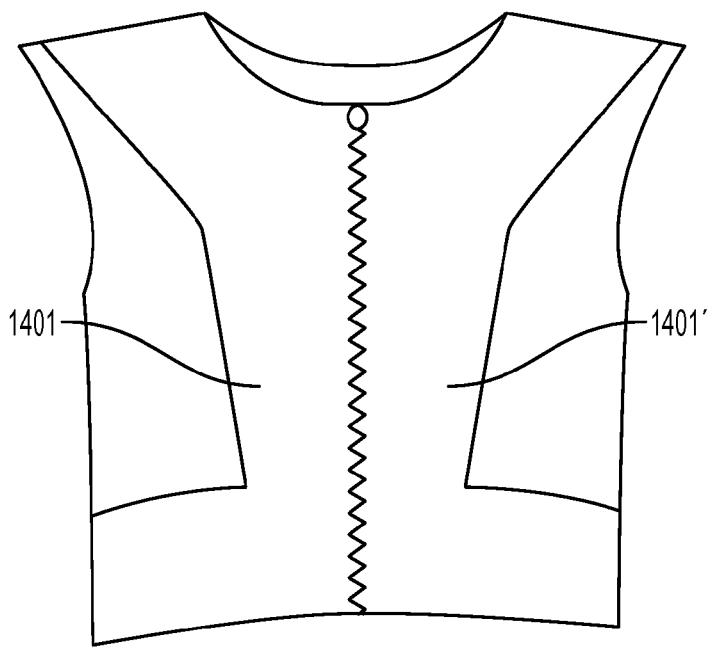
FIGS. 14A and 14B show front and back views, respectively, of an adjustable balance evaluation tool configured as a vest.
Figure 14B:
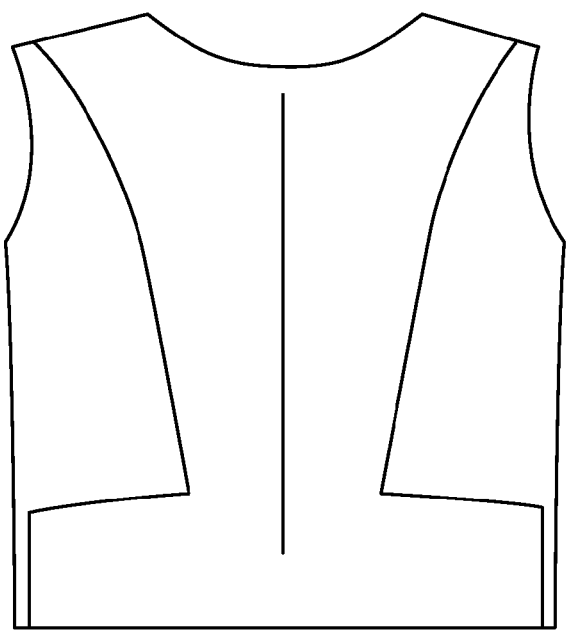

FIGS. 14A and 14B illustrate another variation of an adjustable balance evaluation system configured as a vest, similar to FIGS. 2A-2B and 5B. In FIGS. 14A and 14B, the vest includes attachment regions 1401, 1401' to which one or more weights may be attached. As mentioned above, these regions may include one or more markings indicating where on the garment (relative to the body) the weight is attached.

Figure 15:
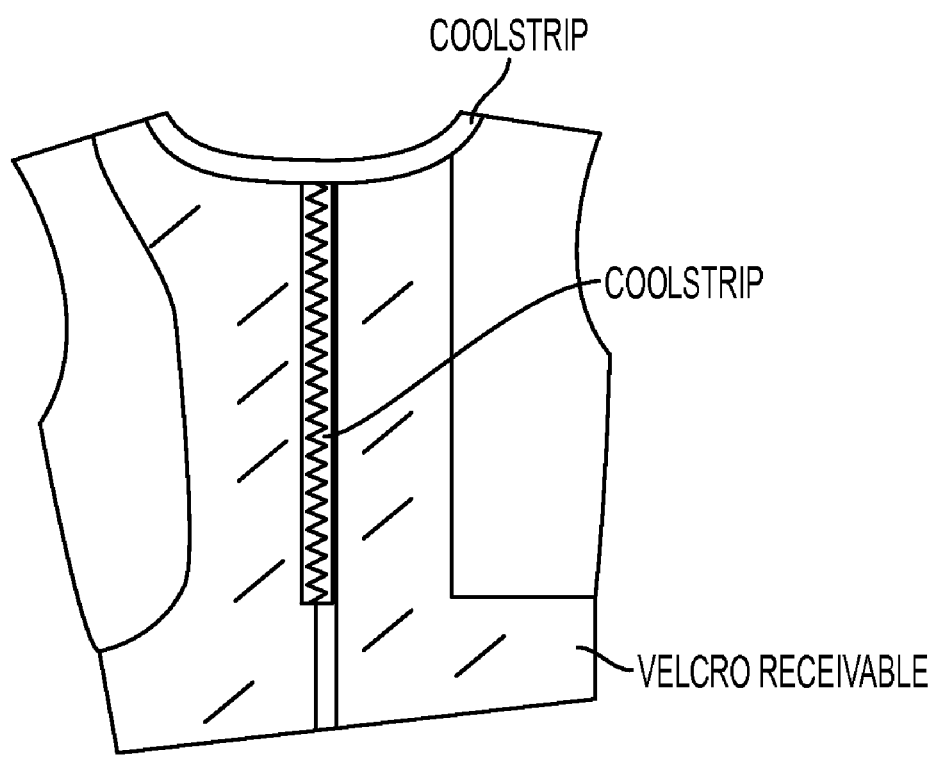
FIG. 15 is an adjustable balance evaluation tool including a cooling component.
Figure 16:
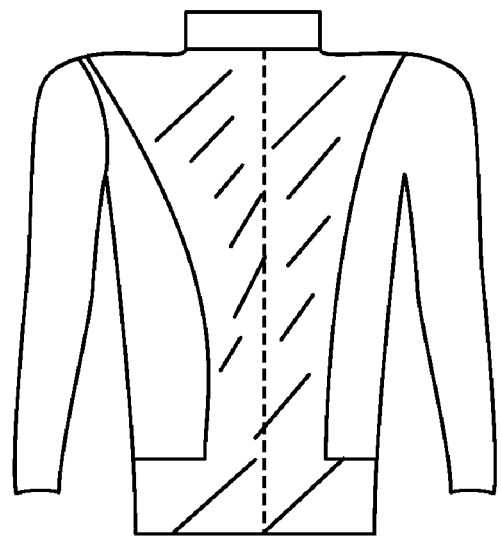
FIG. 16 is an adjustable balance evaluation tool in conjunction with garment shell, configured as a shirt or jacket.

Any of the variations described herein may also include additional elements, including cooling or heating elements. As mentioned, the weight may be configured to provide location-specific therapeutic benefit. In some variations the garment may also include one or more additional elements to provide benefit, including therapeutic benefit. FIG. 15 shows a vest-like adjustable balance evaluation system in which the system includes a cooling feature for cooling the user. In this example, the device includes one or more strips of coolant material ("coolstrips") 1501 along regions of the device. These coolant regions may comprise crystals that can be secured to the garment using the same attachment mechanism used by the weights. For example, the additional element (in this example the cooling strips) may be secured to the garment by a Velcro-type attachment such as that used by the weights. The cooling strips may be a pre-cooled (e.g., frozen) material that is applied after removing it from a freezer or the like. In some variations the cooling strips of material may be secured by other fasteners, including zippers, buttons, etc. The cooling strips may be applied in predetermined locations (e.g., along the periphery, around the neck, etc.), or may be applied in any desired location using a Velcro-type fastener, as just mentioned.

Figure 17:
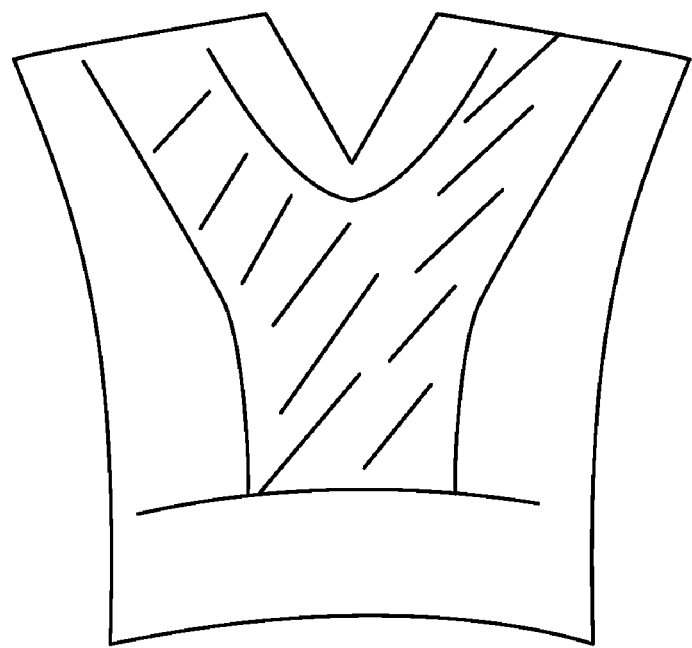
FIG. 17 is another variation of an adjustable balance evaluation tool configured as a yoga garment.

FIG. 15 shows a variation of an adjustable balance evaluation system configured as a jacket. In this example, the jacket includes an inner adjustable balance evaluation system (e.g., straps and belt) such as those shown in FIGS. 7A-7E, as well as an outer shell that covers the straps, belt and any weights. The shell may include a liner. The shell may be secured to the straps and/or belt. FIG. 17 illustrates an example of an adjustable balance evaluation system in which the system is configured as a yoga shirt which may fit over or under the straps and belt region of the adjustable balance evaluation system to which the weights may be attached.

Figure 18A:
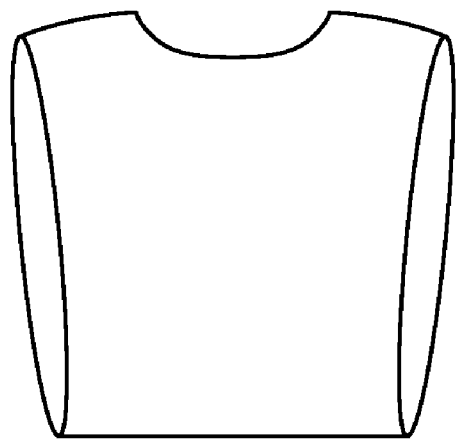
FIGS. 18A and 18B is another variation of an adjustable balance evaluation tool configured as part of a hospital garment.
Figure 18B:
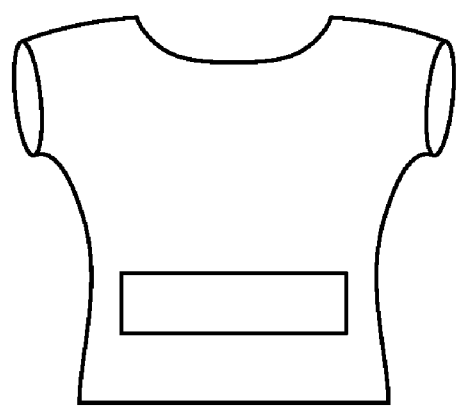
Figure 19:
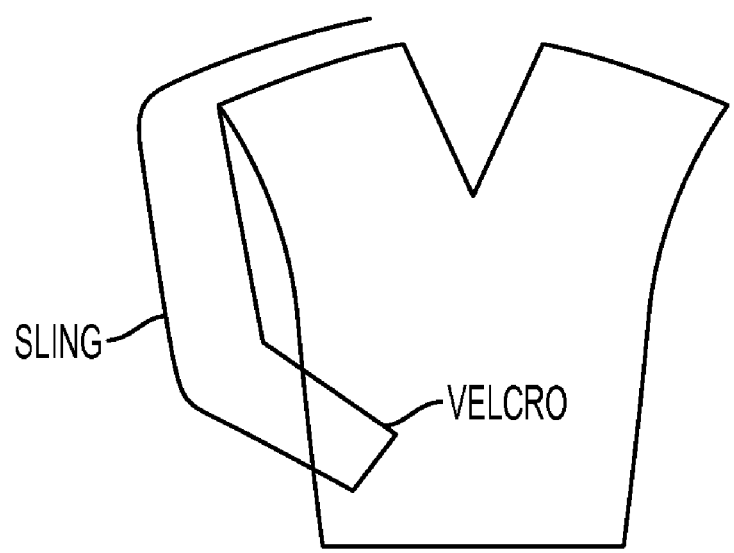
FIG. 19 is another variation of an adjustable balance evaluation tool configured as a sling.
Figure 20:
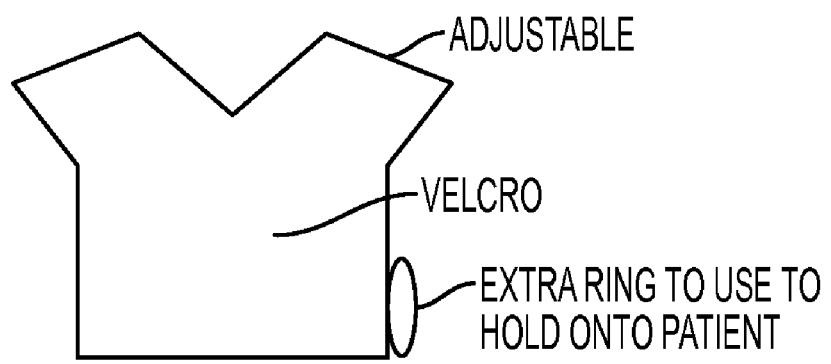
FIG. 20 is another variation of an adjustable balance evaluation tool including a patient support portion.

In some variations the adjustable balance evaluation systems may be configured for use in a hospital or healthcare (e.g., chronic health care) setting. For example, FIGS. 18A and 18B illustrate a hospital-style shirt to which one or more weights may be attached. In addition, the garment may include one or more regions configured to help a third party (e.g., nurse, technician, therapist, caregiver) to hold the wearer securely. For example, in FIG. 18B, the adjustable balance evaluation system is shown to include a belt region adapted to allow a caregiver to more easily grasp and support the subject wearing the device. Similarly, FIG. 20 is an adjustable balance evaluation system including a ring that may be used to hold onto the patient. The majority of the rest of the device includes an outer surface of Velcro-like material for securing a weight as described above. FIG. 19 illustrates another variation of an adjustable balance evaluation system including a sling portion.

Figure 21:
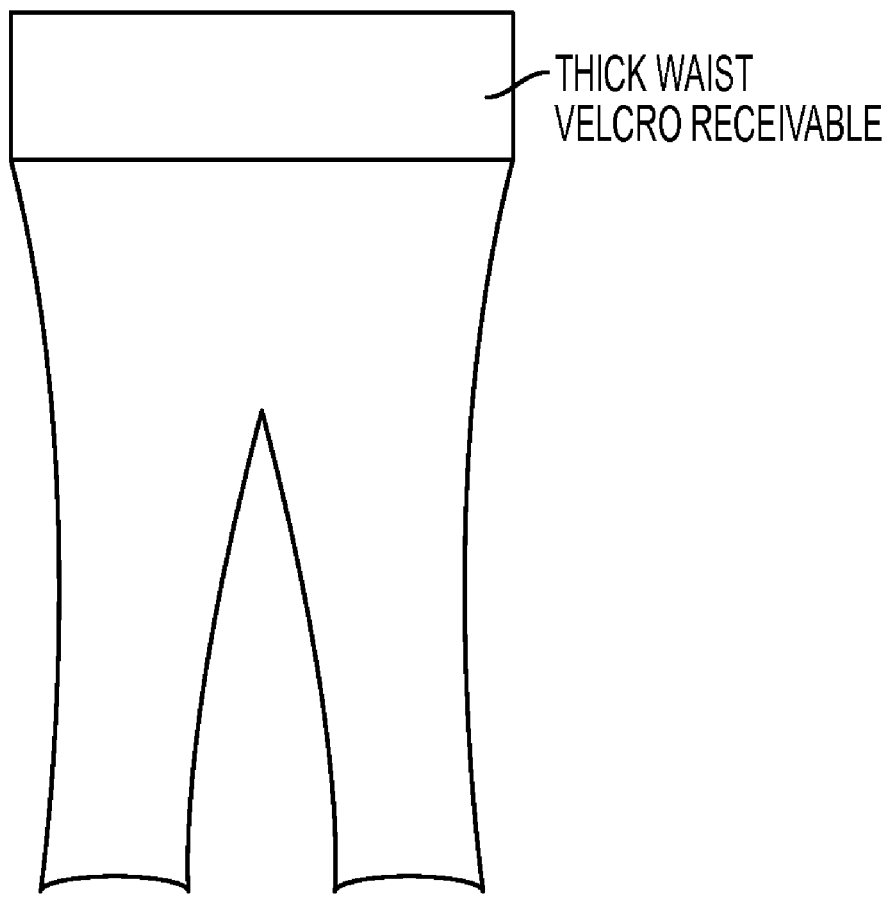
FIG. 21 is another variation of an adjustable balance evaluation tool including a waistband/belt region and pant legs.

FIG. 21 shows another variation of a garment including an adjustable balance evaluation system. In this example, the garment includes a pants region and a belt. The belt is configured so that one or more weights may be positioned on it. The pants may also be configured so that one or more weights may be placed or positioned on it, and secured in position. Although most of the variations described herein are adjustable balance evaluation systems for use with a subject's torso, these systems may be used with other body regions as well, including the legs, feet, arms and head. FIGS. 28A-32, described below, illustrate this point.

Figure 22:
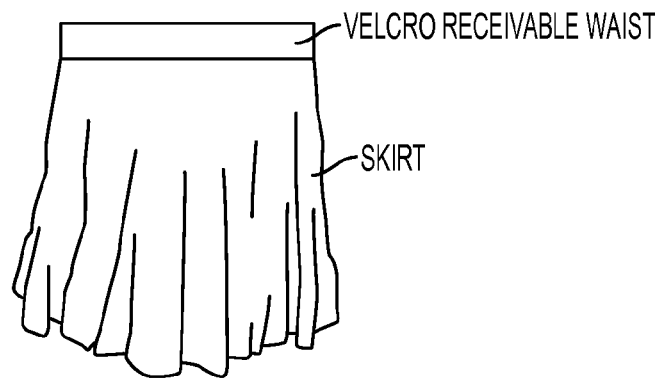
FIGS. 22-25 illustrate different variations of adjustable balance evaluation tools configured as various garments.
Figure 23:
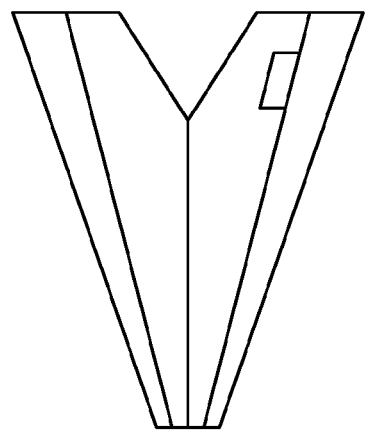
Figure 24:
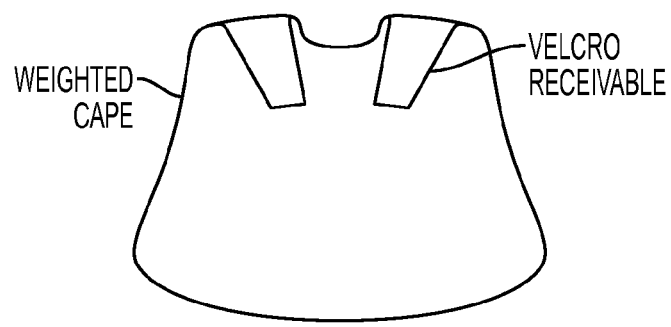
Figure 25:
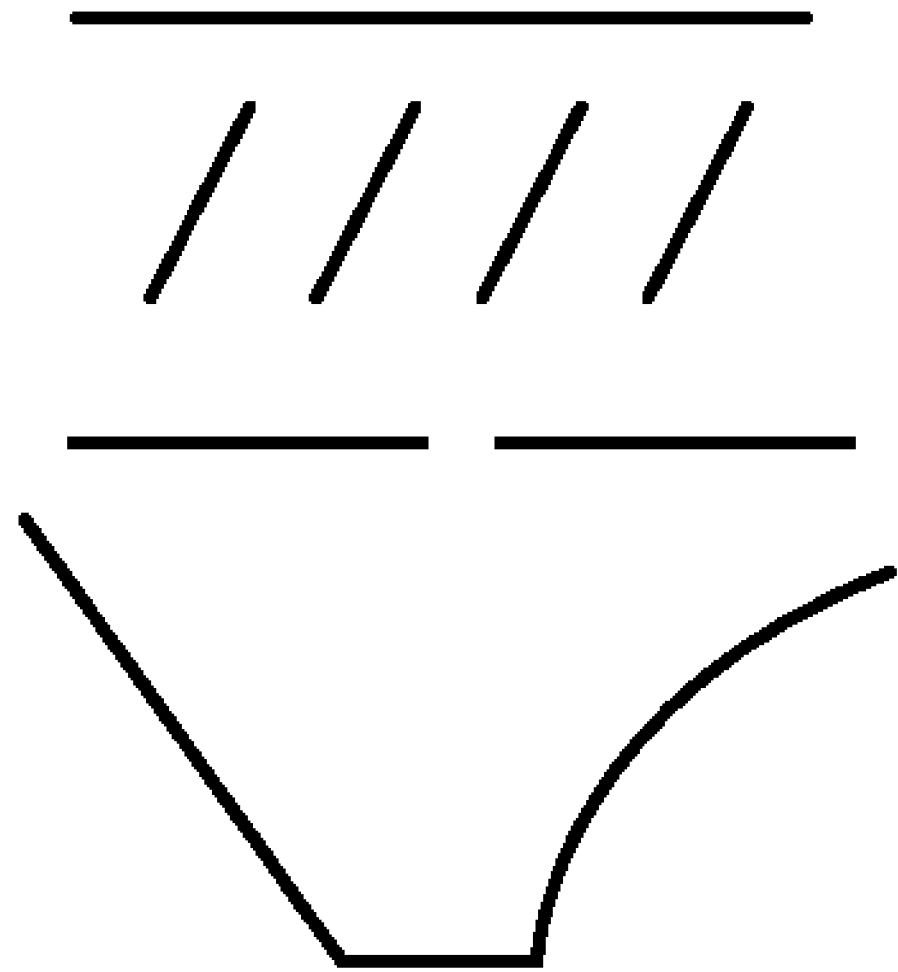

FIGS. 22-25 show additional variations of garments including adjustable balance evaluation systems. For example, FIG. 22 shows a skirt or costume including a belt configured to hold (and to show the position of) one or more weights. FIG. 23 shows a leotard including a pair of straps to which one or more weights may be attached. FIG. 24 illustrates a cape having attachment sites (e.g., near or on the shoulders). FIG. 25 illustrates a pair of underwear (e.g., panties) having a waistband/belt configured to secure one or more weights.

Any of the garment variations described herein may be configured as a customized non-adjustable orthotics as described. Once the correct position and/or weight of the one or more weights has been determined, the garment may have an appropriate weight sewn or otherwise permanently attached in the correct position.

Weighted collars may also be used as part of an adjustable balance evaluation system (or a non-adjustable orthotic). FIG. 26A illustrates a collar configured to attach thin (e.g., ⅛ inch weighted thermoplastic elastomeric gel) weights that can be placed in or upon the collar in non-predetermined positions to impart proprioceptive and sensory input to the subject wearing the device. FIGS. 26B-26D illustrate different variations of weights or weight packets (FIG. 26C) that may be used. Any appropriate fastener may be used. The collar may also be an orthotic that molds around a patient's neck and may extend from the patient's chin to the patient's clavicle.

FIG. 27 illustrates another variation of a weightable belt that may be used. In this variation, the belt is formed of a washable fabric that is marked as described above. The weight may be movably positioned along the belt. For example, the belt may include a magnetic material, to which the weight (which may also be a magnetic material) may be secured.

FIGS. 28A-29 illustrate adjustable balance evaluation systems to be worn on the subject's head. For example, FIG. 28A shows a head cap device (garment) to which strips of tacky fabric (in which light, thin weights can be affixed) along one or more surfaces cover the head either on the inside or outside of the garment. Utilizing the method for determining the improvement in center of gravity control described herein, one may simply observe a subject's head over their shoulder position or head on trunk control to help determine weighting. Based on static and dynamic control, weight may be placed strategically in a non-predetermined location(s) within or upon the flexible cap, headband, or crown encircling all or part of the skull. One variation includes a cap with indicators (e.g., markings). The device or garment could also be made to look like a baseball cap, bonnet, sun hat, hat with a visor. FIG. 28B is an example of a weight that could be attached in or upon the skull cap shown in FIG. 28A by any means already described above. FIG. 29 illustrates one variation of a cranial remolding orthosis for deformational plagiocephaly (DP). Conditions that limit infants' mobility, such as isolated torticollis, hypotonia, and cervical spine anomalies, are also associated with DP. In this variation, a weight may be applied via means already discussed within or upon the device or garment. Devices or garments adapted for use on the subject's head (such as those shown in FIG. 29) may include one or more surfaces for attachment of one or more weights. For example, the outer surface 1201 of the headgear may be a Velcro-like attachment material. Specialized ventilated headwear, helmets, or the like (e.g., helmets that provide additional protection around the ears and nape of the neck) may be adapted for use as adjustable balance evaluation systems and/or non-adjustable orthotics. Devices or garments adapted for use on a subject's head also include, or can consist essentially of, a weighted barrette or a headband to which thin weights or other stimuli described herein can be attached.

Figure 30:
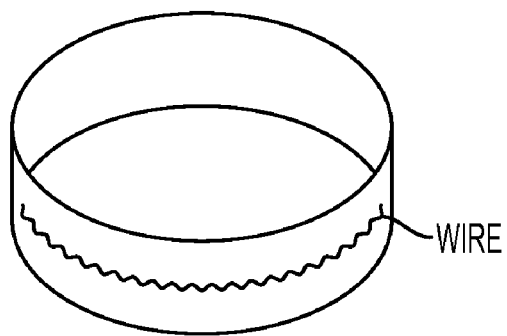
FIG. 30 is an adjustable balance evaluation tool configured as a cuff or bracelet.

In general, the devices and systems described herein may help promote or convey balance. Thus, these devices may be configured as sportswear (e.g., the yoga, golf, etc., outfits), or other variations, include those shown in FIGS. 30-32. For example, FIG. 30 illustrates a bracelet/cuff to be worn on a subject's arm. This bracelet, brace or cuff may be used to hold different amounts of weights that can be secured via a screw, ring, magnet, wire (e.g., sliding them onto the device like an abacus), Velcro, or the like. In some variations the weight may be crimped on to the device. Attachment of weight may help to impart increased weight at a certain spot on the arm to change control of movement/center of gravity control of the arm for tremor control. Thus, in some variations the device may be secured to the body so that it doesn't dramatically change the position of the weight relative to the body. For example, the bracelet may be held to the arm in a particular orientation using an elastic material.

Figure 31:
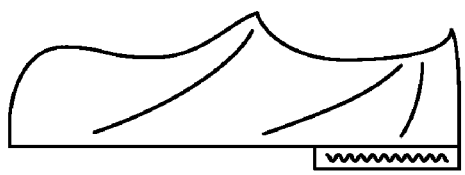
FIG. 31 is an adjustable balance evaluation tool configured as a show.

FIG. 31 illustrates a shoe orthotic to which strips of weight can be applied to the foot or ankle to shift control of the person's foot and guide it medially or laterally. Weight could be introduced through the inside of the heel or at the laces.

Figure 32:
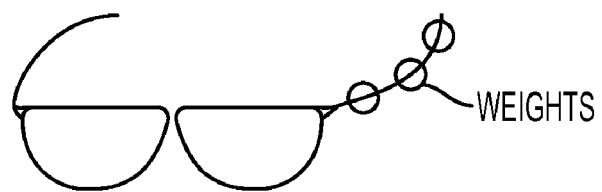
FIG. 32 is an adjustable balance evaluation tool configured as a pair of glasses.

Similarly, FIG. 32 illustrates a pair of glasses to which small sliding weights may be placed along the frame of the glasses to provide a means to change the COG of the head, and/or to improve vision or equilibrium. As suggested already, the weights can be asymmetrical about the head.

This disclosure also includes methods for improving a subject's vision. In these methods, a subject's vision is initially evaluated. This evaluation could be done by a health care provider. After the initial evaluation, a person's vestibular or ocular system is stimulated by one or more stimuli or devices described herein. In some instances, the subject's vestibular or ocular system is stimulated by attaching one or more repositionable stimuli, such as weights, to a garment being worn by the subject, or to eyeglasses, such as those shown in FIG. 32. If, when compared to the initial evaluation of the subject's vision, the subject's vision does not show improvement, the one or more stimuli and/or devices applied to the subject's vestibular system can be adjusted or added to. These steps of comparing and adjusting or adding to the one or more stimuli or devices are repeated until the subject's vision shows improvement when compared to the initial evaluation. In some instances, the improvement in vision occurs while the subject is being stimulated. In other instances, the improvement in vision can occur or persist after the stimuli or device is no longer stimulating the subject.

The devices and systems described herein may also be configured as an orthotic to be worn on a subject's leg or configured as a prosthetic leg or limb. As with the above-described devices, weights can be attached to the orthotic or prosthesis by a screw, ring, magnet, wire (e.g., sliding them onto the device like an abacus), hook and loop fastener (e.g., Velcro) or the like. In some variations the weight may be crimped on to the orthotic or prosthesis. In other variations, the orthotic or prosthesis may be formed to be weighted in one or more positions (i.e., the orthotic or prosthesis includes the weight). Attachment of weight may help to impart increased weight at a certain spot on the leg to change control of movement or center of gravity for tremor control. By promoting or conveying balance, the orthotic or prosthesis can improve a subject's ability to walk, stand, or run.

FIGS. 34-38 show a garment, such as a vest, with a relatively rigid back support. The materials, use of weights, and the methods for providing the weights on or to the garment, all as described above, can be used.

Figure 35:
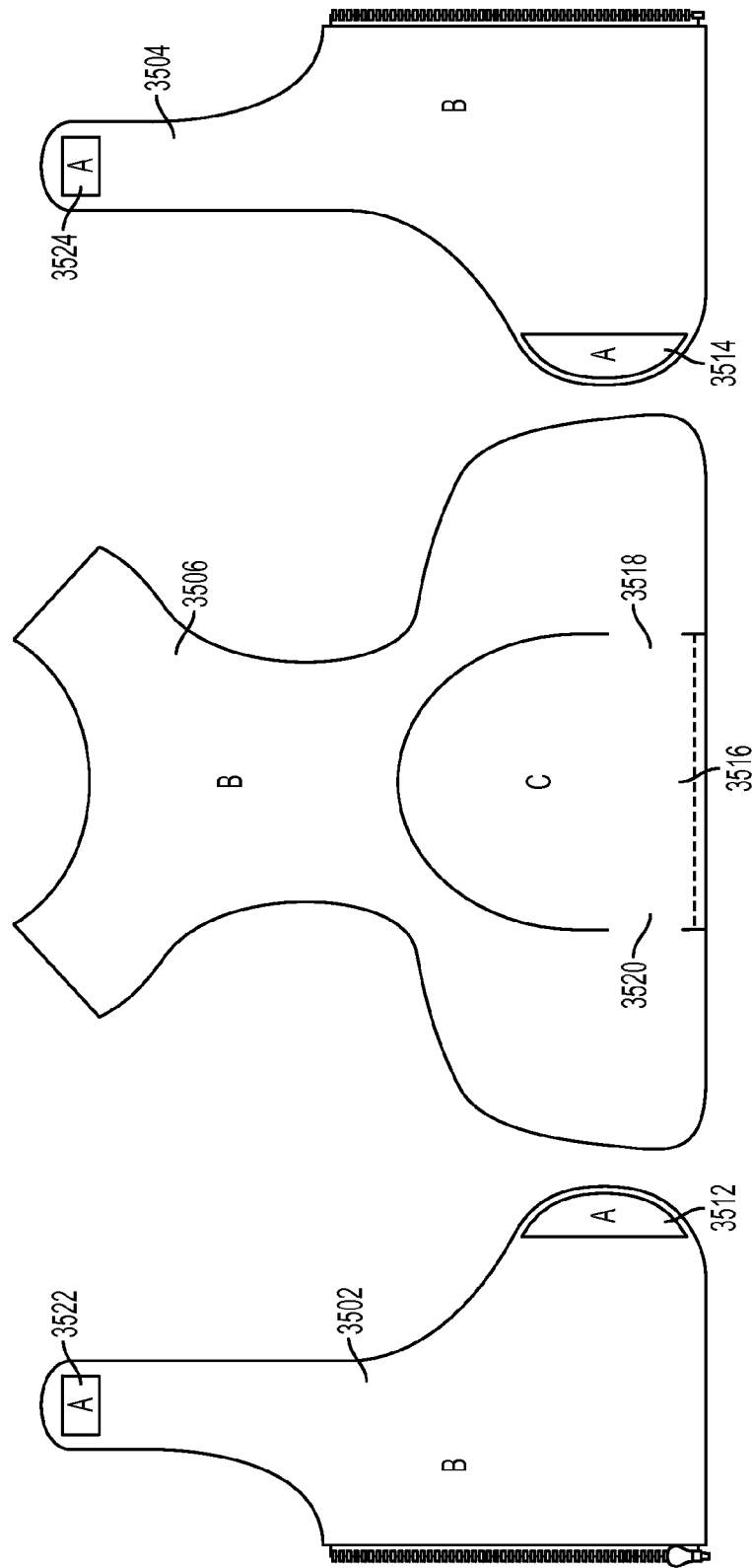

FIG. 35 illustrates the inside of a garment that can provide additional back support. The garment can be adjustable to fit patients of different sizes. The garment can be of unitary design or be made of multiple components. FIG. 35 illustrates a garment made of multiple components. Side components 3502 and 3504 illustrate components that attach to a back component 3506. Side components 3502 and 3504 can attach to back component 3506 by hook and loop material (e.g., Velcro), buttons, zippers, or other ways of connecting garment components as described herein. Locations 3512, 3522, 3514, and 3524 illustrate where Velcro-type hook material can be located on side components 3502 and 3504 to connect side components 3502 and 3504 to back component 3506. Buttons, button holes, or zippers can also be used. Components 3502, 3504, and 3506 can be mostly or entirely covered with unbroken loop material that is receptive to Velcro-type hook material for placement of one or more stimulus.

Figure 36:
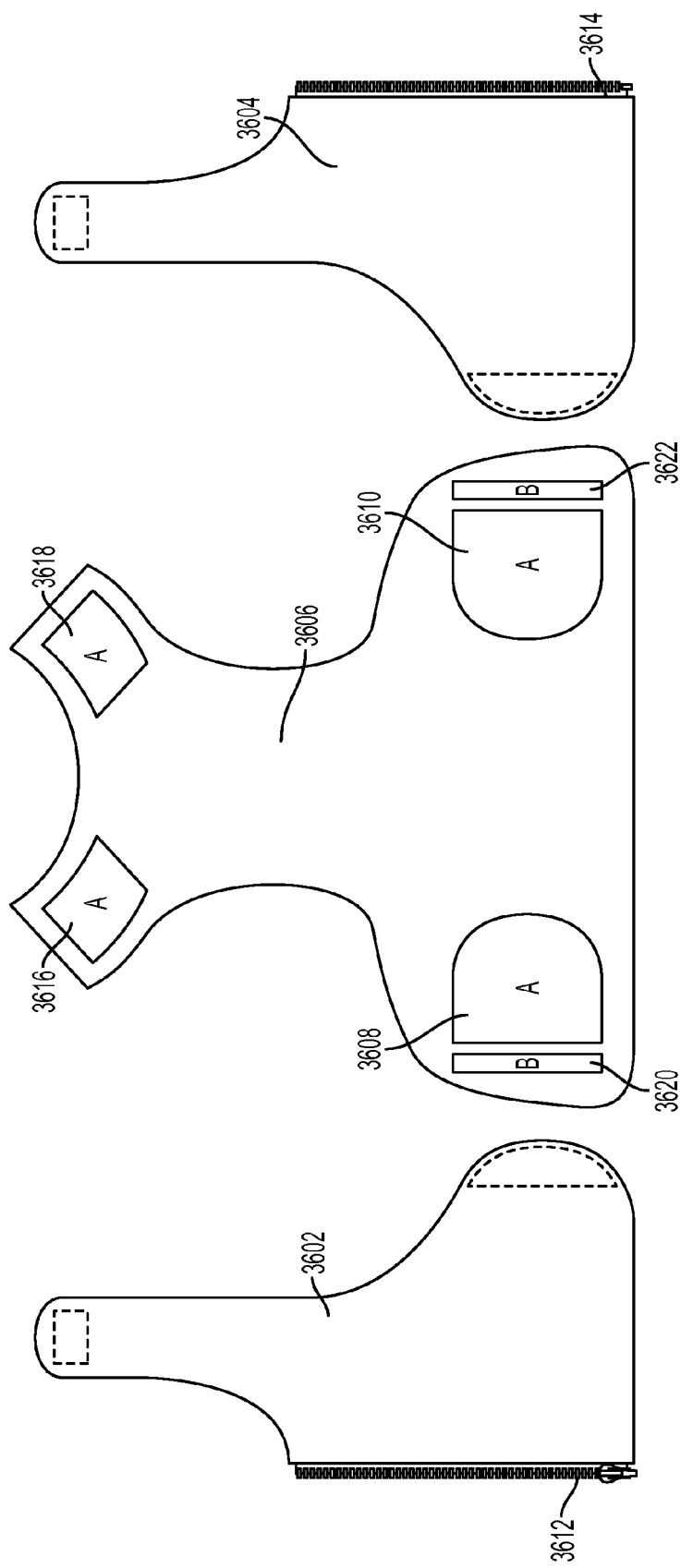

FIG. 36 illustrates the outside of the garment of FIG. 35. Back component 3606 (which is the outside of back component 3506 in FIG. 35) can include unbroken loop material on the outside at locations 3608, 3616, 3610, and 3618, so that side components 3502 and 3504 (side components 3602 and 3604 in FIG. 36 illustrate the outside of side components 3502 and 3504) can attach to back component 3606 via the Velcro-type hook material at locations 3512, 3522, 3514, and 3524. As mentioned above, other methods, including, but not limited to, buttons and zippers, can also be used. Back component 3606 can also include some Velcro-type hook material at, for example, locations 3620 and 3622 that will connect to the unbroken loop material on 3502 and 3504. Side components 3602 and 3604 can be connected to each other via zippers 3612 and 3614.

Referring also again to FIG. 35, back component 3506 includes a relatively rigid insert that supports the wearer's back. Pocket 3516 is designed to receive and hold the insert. The insert may be sown into pocket 3516, or pocket 3516 can be designed so that the insert is removable, thereby allowing different inserts of different shapes, different materials, or different weights to be inserted. The insert can have a variety of shapes designed to support the back. For example, the insert may have shapes such as those shown by insert 3726 in FIG. 37 or insert 3402 in FIG. 34. As indicated in the figures, the insert can have a wider portion at the bottom and narrower at the top. The shape can be considered generally triangular, or generally pentagonal (like a home plate), but with rounded corners, and if desired, some contour to one or more of the sides. The insert can be relatively rigid, i.e., more rigid than the garment material, but have sufficient flexibility to contour to the wearer's back. The insert can be made of materials that range in degree of flexibility from flexible enough to contour to a wearer's back to being a stiff, relatively inflexible customized mold formed to fit an individual's back. The insert may be made of any material suitable for providing back support, including, but not limited to, acrylics, high density polyethylene (HDPE), low density polyethylene (LDPE), polycarbonates, thermoplastic polymers, foams, etc.

Pocket 3516 has openings 3520 and 3518 on each side. These openings are also shown as openings 3804 and 3806 on FIG. 38. FIG. 38 illustrates another view of the inside of the garment where side components 3820 and 3822 are connected to back component 3824. Arm openings 3816 and 3818 are for the wearer's arms. Belt 3802 is fed through one of openings 3804 and 3806 and then around the outside of the insert (shown in dashed lines) contained in pocket 3810 and out the other opening. FIG. 37 illustrates the belt in further detail. Belt 3702 includes back 3704 that goes around the insert in the pocket. Back 3704 can be made of a vented, elastic material or a relatively inelastic material, and can be made of the same material as the rest of the belt. Back 3704 can be the same size as sides of belt 3706 and 3708 or can be larger, as illustrated in FIG. 37. Sides of belt 3706 and 3708 can be made of an elastic or inelastic material and can have unbroken loop material on the outside. The belt may be placed inside a garment and sides 3706 and 3708 can be pulled through slots 3806 and 3804 in the garment.

Ends 3710 and 3712 of belt 3702 include Velcro-type hook material on the inside at, for example, positions 3714 and 3716. Sides 3706 and 3708 of the belt can be connected to a front panel 3718 that contains insert 3720 by, for example, threading ends of belt 3710 and 3712 through loops 3722 and 3724 on front panel 3818. Insert 3720 can be sown into front panel 3718 or front panel 3718 can have a resealable pocket so that insert 3720 can be removable. Insert 3720 may be made of any material suitable for providing back support, including, but not limited to, acrylics, high density polyethylene (HDPE), low density polyethylene (LDPE), polycarbonates, thermoplastic polymers, foams, etc. Once ends of belt 3710 and 3712 are fed through loops 3722 and 3724, Velcro-type hook material at locations 3714 and 3716 can be connected to unbroken loop material on the outside of sides 3706 and 3708 of the belt. When the belt is wrapped around a subject and the ends of belt 3710 and 3712 are fed through loops 3722 and 3724, the connection of the Velcro-type hook material at 3714 and 3716 to unbroken loop material on the outside of sides of belt 3706 and 3708 secures the belt in place.

The rigid or relatively rigid back support can be used with other types of garments, such as those shown above, e.g., a belt without an upper portion with arm openings.

One or more stimulus can be attached to the unbroken loop material on the inside of the garment by Velcro-type hook material or any other method of attaching stimulus herein described. The stimulus can be of any type described herein. The stimulus can also be placed on the outside of the garment. The garment can, but need not, include a position reference system for marking the position of one or more stimulus, such as that shown in U.S. Pat. No. 7,156,792, which is incorporated herein by reference for all purposes.

Another aspect of this disclosure is directed to devices for stimulating a subject's vestibular system. Devices for stimulating a subject's vestibular system can include any of the devices described herein, including multiple devices in combination.

Also included in this disclosure are methods for improving a subject's vestibular system. In these methods, a subject's vestibular system is initially evaluated. Generally, this evaluation can be done by a health care provider. Next, the subject's vestibular system is stimulated by one or more stimuli or devices described herein. In some instances, the subject's vestibular system is stimulated by attaching one or more repositionable stimuli to a garment, orthotic, or device being worn by the subject. The garment, orthotic, or device may be any of the garments, orthotics, or devices described in this disclosure. Then, the subject's vestibular system is evaluated again. If, when compared to the initial evaluation of the vestibular system, the subject's vestibular system does not show improvement, the one or more stimuli and/or devices applied to the subject's vestibular system can be adjusted or added to. These steps of comparing and adjusting or adding to the one or more stimuli or devices are repeated until the subject's vestibular system shows improvement when compared to the initial evaluation. In some instances, the improvement in the vestibular system occurs while the subject is being stimulated. In other instances, the improvement in the vestibular system can persist or occur after the stimuli or device is no longer stimulating the subject.

In addition to methods described above for improving a subject's vestibular system and vision, this disclosure also includes similar methods for improving speech (including, but not limited to, clarity, vocal ataxia, projection, and timing), cognition (including, but not limited to, time spent on a task, attention span, reading, spelling, and math), proprioception, walking, running, standing, trunk control, spinal reflexes, coordination of upper and lower trunk, upper extremity control, finger tapping, handwriting, lower extremity control, general coordination, sea sickness, latency of response from perturbation from the ground up or the trunk down, swallowing, and kyphosis. In some instances, the improvement occurs while the subject is being stimulated. In other instances, the improvement occurs after the stimuli or device is no longer stimulating the subject.

Figure 33A:
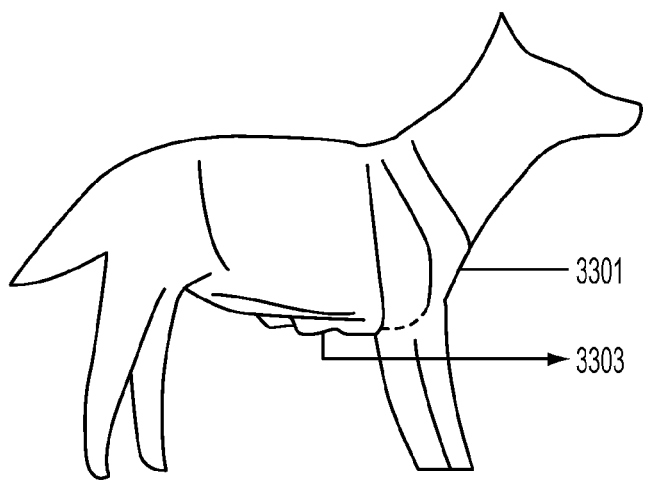
FIGS. 33A and 33B show variations of adjustable balance evaluation tools configured for use with non-human animals.
Figure 33B:
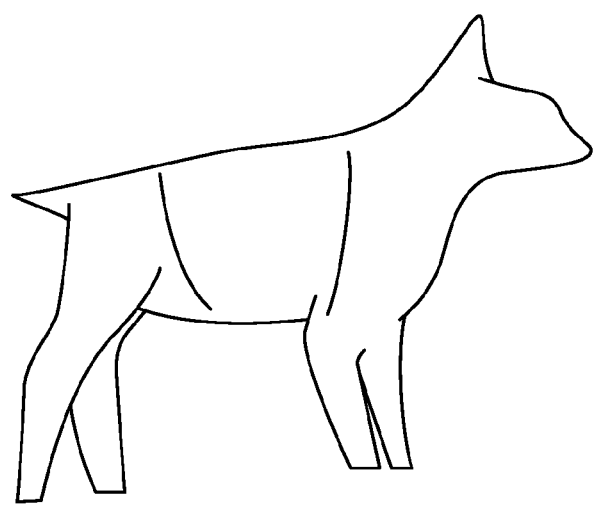
Figure 33C:
FIGS. 33C and 33D illustrate a weight and weight packet that may be used with an adjustable balance evaluation tool including the tool (system) illustrated in FIGS. 33A and 33B.
Figure 33D:

Any of the devices, systems and methods described herein may be used in humans, and also in non-humans, particularly non-human vertebrates. For example, FIGS. 33A-33B illustrate variations of an adjustable balance evaluation system that may be used for a dog. FIG. 33A shows a dog wearing strap 3301 and Velcro device 3303 to which one or more weights may be attached. An alternative variation is shown in FIG. 33B. FIGS. 33C and 33D illustrate weight 3305 and weight packet 3307 that may be used with the variations shown in FIGS. 33A and 33B.

Although illustrative variations of the present invention have been described above, it will be evident to one skilled in the art that various changes and modifications may be made without departing from the invention. For instance, variations of the present invention may include weighted devices on the lower extremities or any other area of the body. In addition, the present invention may include the use of the procedures described herein for therapy, repeating the procedures as often as necessary, as the amount or placement of the weights may change over time. It is intended in the following claims to cover all such changes and modifications falling within the true scope and spirit of the invention.

What is claimed is:

1. An apparatus for stimulating a patient's sensory system, comprising:
 a garment made of a flexible and wearable material, and configured to be worn on the patient's torso and comprising an inner and an outer surface, the garment capable of receiving one or more stimuli over a plurality of immediately adjacent and continuous positions;
 one or more repositionable stimuli capable of sensorially stimulating the patient and configured to attach to the garment; and
 at least one removable insert in an insert pocket within the garment for supporting the patient's back, the insert comprising a shape to physically support the patient's back and being relatively rigid compared to the garment material.

2. The apparatus of claim 1, further comprising belt.

3. The apparatus of claim 2, wherein the belt further comprises means for coupling to a front panel for accommodating a removable insert.

4. The apparatus of claim 2, wherein the belt wraps around the insert in the garment, wherein the belt is removably threaded through a pair of openings defined on either side of the insert pocket.

5. The apparatus of claim 1, wherein the apparatus is comprised of at least two side components and a back component removably coupled together at a plurality of immediately adjacent and continuous positions.

6. A method of improving a subject's vision, comprising:
 (a) evaluating the subject's vision;
 (b) stimulating the subject's ocular system by attaching one or more repositionable stimuli to a device worn by the subject;
 (c) reevaluating the subject's vision;
 (d) comparing the subject's vision in (c) to the subject's vision in (a); and
 (e) repeating (b)-(d) until the subject's vision shows improvement after the comparison in (d).

7. The method of claim 6, wherein the device is a garment.

8. The method of claim 7, wherein the garment is cap, headband, barrette, or hat.

9. The method of claim 7, wherein the garment is configured to fit the subject's torso.

10. The method of claim 6, wherein the device is a pair of eyeglasses or an eyeglass frame.

11. A method of improving a subject's vestibular system, comprising:
 (a) evaluating the subject's vestibular system;
 (b) stimulating the subject's vestibular system by attaching one or more repositionable stimuli to a device worn by the subject;
 (c) reevaluating the subject's vestibular system;
 (d) comparing the subject's vestibular system in (c) to the subject's vestibular system in (a); and
 (e) repeating (b)-(d) until the subject's vestibular system shows improvement after the comparison in (d).

12. The method of claim 11, wherein the device is a pair of eyeglasses or an eyeglass frame.

13. The method of claim 11, wherein the device is a garment.

14. The method of claim 13, wherein the garment is configured to be worn on the subject's torso.

15. The method of claim 13, wherein the garment is a cap, headband, or hat.

16. The method of claim 11, wherein the device is an orthotic configured to fit the subject's torso.

17. The method of claim 11, wherein the device is a prosthesis.

18. The method of claim 17, wherein the prosthesis is a prosthetic limb.

19. The method of claim 18, wherein the prosthetic limb is a prosthetic leg.

20. The method of claim 11, wherein the one or more repositionable stimuli comprise one or more weights, wherein the one or more weights combine to weight between about 0.2% to about 2% of the subject's body weight.

* * * * *